US011622257B1

(12) United States Patent
Mars et al.

(10) Patent No.: US 11,622,257 B1
(45) Date of Patent: Apr. 4, 2023

(54) METHODS AND APPARATUS FOR PRESENCE MONITORING

(71) Applicant: Proxy, Inc., San Francisco, CA (US)

(72) Inventors: Denis Mars, San Francisco, CA (US); Simon Ratner, San Francisco, CA (US)

(73) Assignee: Proxy, Inc., San Francisco, CA (US)

( * ) Notice: Subject to any disclaimer, the term of this patent is extended or adjusted under 35 U.S.C. 154(b) by 134 days.

(21) Appl. No.: 17/326,197

(22) Filed: May 20, 2021

Related U.S. Application Data

(60) Provisional application No. 63/029,004, filed on May 22, 2020, provisional application No. 63/027,769, filed on May 20, 2020, provisional application No. 63/027,774, filed on May 20, 2020.

(51) Int. Cl.
| | |
|---|---|
| *H04W 8/06* | (2009.01) |
| *H04L 9/40* | (2022.01) |
| *H04L 9/12* | (2006.01) |
| *H04L 9/32* | (2006.01) |
| *H04W 12/06* | (2021.01) |

(52) U.S. Cl.
CPC ............... *H04W 8/06* (2013.01); *H04L 9/12* (2013.01); *H04L 9/32* (2013.01); *H04L 9/3297* (2013.01); *H04L 63/0876* (2013.01); *H04L 63/123* (2013.01); *H04W 12/06* (2013.01)

(58) Field of Classification Search
CPC .......... H04W 8/06; H04W 12/06; H04L 9/12; H04L 9/32; H04L 63/0876; H04L 63/123; H04L 9/3297
See application file for complete search history.

(56) References Cited

U.S. PATENT DOCUMENTS

| | | | | |
|---|---|---|---|---|
| 9,043,602 | B1 * | 5/2015 | Krieger ................ | H04W 12/06 713/181 |
| 2015/0358322 | A1 * | 12/2015 | Krieger ............... | H04L 63/0838 713/181 |
| 2018/0234839 | A1 * | 8/2018 | Tenny .................. | H04W 12/10 |
| 2019/0098505 | A1 * | 3/2019 | Mars .................... | H04L 63/102 |

* cited by examiner

*Primary Examiner* — Dominic E Rego

(57) ABSTRACT

A method for a system includes receiving with a first transceiver of a first smart device, an advertisement signal from a stationary beacon, outputting with the first transceiver of the first smart device, a first ephemeral ID that is not permanently associated with the first smart device, to the stationary beacon, receiving with the first transceiver of the first smart device, a beacon identifier from a stationary beacon, outputting with a second transceiver of the first smart device, the first ephemeral ID, a first user identifier and the beacon identifier to an authentication service, storing in an association log in the authentication service, the first ephemeral ID, the first user identifier and the beacon identifier, and storing in a beacon log in the authentication service, a log of the stationary beacon including the first ephemeral ID.

20 Claims, 19 Drawing Sheets

METHODS AND APPARATUS FOR PRESENCE MONITORING

The present invention claims priority to and is a non-provisional of U.S. Pat. App. No. 63/027,769 filed May 20, 2020, a non-provisional of U.S. Pat. App. No. 63/029,004 filed May 22, 2020, and a non-provisional of U.S. Pat. App. No. 63/027,774 filed May 20, 2020. These applications are incorporated by reference herein, for all purposes.

BACKGROUND

This invention relates generally to systems, methods and devices for first party identification and more particularly to systems, methods and devices for a universal ID.

Presently, attempts to create what the inventors refer to as a universal identification (ID) signal for an individual, have involved frameworks or underlying models in which the burden of implementing the signal—broadcasting it and ensuring that devices detect it—rests on the individual. This task of creating a personal signal, or what the inventors refer to as a transponder or beacon, is beyond the technical domain of the vast majority of users. This is one of the barriers that has prevented the growth of a universal identification signal for individuals, universal in the sense that the signal is not tied to or detectable only by a specific manufacturer, social media or network provider, or company.

One of the inventors' goals of a universal identification signal is to allow a user to identify and interact with a variety of physical world devices or objects by different manufacturers in a manner that allows for strict data control, security, and privacy. In contrast, current user ID models follow a "silo" model. In typical silo models, users emit a specific ID signal via a specific application on a specific device, such as from a smart phone, and the specific ID signal is only detectable by a specific entity, such as an appliance manufacturer, a car manufacturer, or online social media provider, or the like. The specific IDs are thus not universal, for example a Hilton user ID cannot be used for boarding a United Airlines flight. These siloed systems do not provide sufficient mapping to physical, real world environments and spaces that is needed to be useful, safe, and secure.

The inventors believe the silo model of user identification signals where each vendor, each hotel, each apartment, and the like is highly disadvantageous to users and more importantly to their smart devices. Some disadvantages include that the multiple applications take up large portions of the memory in smart devices, crowding out memory for photos, videos, other applications, and the like; another disadvantage is that when executing more than one of these silo applications, the performance of the smart device is impacted because there are large amounts of data that need to be cached for each of the programs, and switching between programs often become sluggish; another disadvantage is that having a large number of applications running at the same time can cause memory management problems in the user's smart device, causing crashes and other anomalous behaviors; and the like. Accordingly, the inventors believe the silo model often adversely affects the performance of smart devices.

There are some implementations, presently in limited use, that essentially leverage one online identity or profile to interact with various types of devices. Besides the security and data control/privacy concerns this raises, such single online personas do not truly reflect how individuals behave or act in the real, physical world. Human interactions with physical environments have developed over millennia, as such, it should not be expected that this behavior be reflected in online personas.

Other factors that have prevented universal or even quasi-universal signal technology from widespread adoption include generally a lack of motivation from manufacturers and companies to create their own apps, portals, back-end infrastructure, and so on, that would be needed to implement a signal or beacon framework with their customers. Again, this leads to a siloed approach that is simply not worth the expense and maintenance for many entities. Returning to the first point of placing too much of the technical burden of implementing universal signals on the users, it is certainly possible to create sensing points in an environment, but this framework requires that users modify their behavior, act in a different way and actually require that additional actions be taken by users. What is needed is a framework that does not require this of users and where the physical world or environment be essentially smarter and place minimal additional burden on the users to allow for seamless natural interactions.

SUMMARY

This invention relates generally to systems, methods and devices for first party identification and more particularly to systems, methods and devices for a universal ID. With embodiments of the present invention, storage memory of smart-devices is increased due to the reduced number of applications and programs that need to be stored, and the performance of the smart-devices is increased due to the lower number of applications required to operate simultaneously, while still providing the functionality desired by a user. In various embodiments, the reduction in demand on smart-device resources provide advantages to a smart device in terms of amount of free memory available for applications and the speed and efficient performance of applications running upon the smart device.

One aspect disclosed is a method of enabling a universal identifier signal, also referred to as a universal personal transponder (e.g. transceiver), using a beacon apparatus and a detector apparatus that performs as a scanner or sensor. In various embodiments, the beacon may be a smartphone, wearable device or other smart apparatus carried by a user, and broadcasts what is referred to as an ephemeral identifier. This ephemeral ID is typically enabled by an application installed on the smartphone or smart apparatus. The ephemeral ID is then detected or sensed by a detector device which may be constantly scanning the environment for ephemeral IDs and related data. In various embodiments, the detector can be built into a wide variety of devices, such as appliances, electronic equipment, public kiosks, controlled access points and the like. As described below, the detector device resolves the ephemeral ID to a user of a specific beacon apparatus, that is, the ephemeral ID is matched to a specific registered individual or user. A dedicated server, typically operated by a (e.g. universal) signal service provider, receives at least a portion of the ephemeral ID and verifies an access-control list (i.e. determines stored user data) associated with the specific registered user associated with the ephemeral ID. A first set of user data is then transmitted from the dedicated server to the detector device, such as a controlled access point (e.g. door lock, security door, turnstile, security system, elevator, gate), a coffee machine, kitchen appliance, TV monitor, point of sale device, loyalty card kiosk, automobile, appliance, vending machine, environmental controls, etc. The detector device then performs operations based upon the first set of user data to enable substantive and meaningful interactions with the beacon (i.e., the user), such as unlocking a lock, turning on lights, registering the user, or the like. In some embodiments, the actions required by the beacon device are reduced or minimized and the majority of the operations are taken on by the detector device. That is, the user and the user's smartphone or smart device does not need to perform any proactive operations or acts in order to have the user's universal ID signal be recognized by the door lock or have meaningful interaction with the door lock, such as unlocking the door for the user. In other embodiments, the beacon device may perform some of the access functions with the dedicated server automatically, without specific user interaction.

In another aspect of the invention, a system for implementing a universal personal transponder environment includes a beacon apparatus carried by a user that includes universal personal ID transponder software. The user enters an environment or space that has one or more scanner devices which are constantly scanning for a universal ID signal being emitted by the beacon by virtue of the transponder software. The detection of the universal ID signal occurs with minimal operations or actions needed by the user or the beacon apparatus. The software module on the beacon enables interaction with nearly any type of scanner device that has the necessary transponder software and hardware connectivity component. A dedicated service or server has a database for storing various types of data and multiple software modules for implementing the universal personal transponder environment. In some cases, the server may be operated and owned by a universal personal transponder service provider (SAAS) which operates the system for the benefit of the user and the scanner or detector device manufacturers or operators which may include a wide variety of device from door locks to electronic equipment. In other cases, the server may be operated and/or owned by a detector device manufacturer (e.g. controlled access point) and still be compatible with the universal ID signal from the universal ID software. In some embodiments, the majority of the processing and proactive steps needed to implement the environment is done by the scanner device which queries or monitors the beacon (e.g., smartphone) for ephemeral ID data, communicates with the server, and performs a responsive physical action. In various embodiments, the beacon also performs some steps to ensure security and authentication of the user via biometric scanner, password, or the like. In some embodiments, the burden of initiating the process and establishing a session is performed by the scanner device sensing the ephemeral ID.

According to one aspect of the invention, a method is described. One process includes scanning with a short-range transceiver in a first device for ephemeral ID signals within a geographic region proximate to the first device, and detecting with the short-range transceiver, an ephemeral ID signal output from a user device, wherein the ephemeral ID signal does not include personally identifiable information of the user. One method includes transmitting with a wide-area network communication unit in the first device, at least a portion of the ephemeral ID signal and a first identifier associated with first device to a remote server associated with the ephemeral ID signals and receiving with the wide-area network communication unit, a first reply from the remote server in response to the portion of the ephemeral ID signal and to the first identifier. One technique includes providing an electronic authorization signal to a first external unit coupled to the first device in response to the first reply, wherein the first external unit is configured to perform a first physical action in response to the first reply.

According to another aspect of the invention, a system including a first device is disclosed. In one apparatus, the first device includes a short-range transceiver configured to capture ephemeral ID signals within a geographic region proximate to the first device and configured to detect an ephemeral ID signal output from a user device, wherein the ephemeral ID signal does not include personally identifiable information of the user. In another apparatus, the first device includes a wide-area network interface configured to transmit at least a portion of the ephemeral ID signal and a first identifier associated with first device to a remote server associated with the ephemeral ID signals and configured to receive a first reply from the remote server in response to the portion of the ephemeral ID signal and the first identifier associated with first device. In yet another apparatus, the first device includes an output unit configured to provide an electronic authorization signal to a first external unit coupled to the first device in response to the first reply, wherein the first external unit is configured to perform a first physical action in response to the first reply.

According to one aspect, a system for monitoring presence is described. An apparatus may include a plurality of stationary beacons within a physical region, wherein a stationary beacon from the plurality of stationary beacons includes, a short-range transceiver configured to transmit a unique advertisement signal to a plurality of smart devices, wherein the plurality of smart devices includes a first smart device and a second smart device, wherein the short-range transceiver is configured to receive a plurality of ephemeral IDs that are not permanently associated with the plurality of smart devices, wherein the plurality of ephemeral IDs includes a first ephemeral ID from the first smart device and a second ephemeral ID from the second smart device, wherein the short-range transceiver is configured to transmit a unique beacon identifier to the plurality of smart devices. A stationary beacon may include a memory coupled to the first short-range transceiver, configured to store stationary beacon data including: the first ephemeral ID, a first time associated with receipt of the first ephemeral ID, the second ephemeral ID, and a second time associated with receipt of the second ephemeral ID, a processor coupled to the short-range transceiver and the memory, and a wide-area interface coupled to the memory, wherein the wide-area interface is configured to transmit the stationary beacon data to an authentication service. A device may include an authentication service coupled to the plurality of stationary beacons and to the plurality of smart devices, wherein the authentication service is configured to store the stationary beacon data, wherein the authentication service is configured store association data comprising associations among the plurality of ephemeral IDs, the plurality of smart devices and unique beacon identifiers, wherein the authentication service is configured to receive an alert notice from the first smart device, wherein the authentication service is configured to identify the stationary beacon in response to the alert notice and to the association data, wherein the authentication service is configured to determine the second ephemeral ID in response to the stationary beacon data, wherein the authentication service is configured to determine the second smart device in response to the second ephemeral ID and to the association data, and wherein the authentication service is configured to provide an exposure notice to the second smart device.

According to another aspect, a method for a system is described. A technique may include receiving with a first transceiver of a first smart device, an advertisement signal from a stationary beacon, outputting with the first transceiver of the first smart device, a first ephemeral ID that is not permanently associated with the first smart device, to the stationary beacon, and receiving with the first transceiver of the first smart device, a beacon identifier from a stationary beacon. A process may include outputting with a second transceiver of the first smart device, the first ephemeral ID, a first user identifier and the beacon identifier to an authentication service, storing in an association log in the authentication service, the first ephemeral ID, the first user identifier and the beacon identifier, and storing in a beacon log in the authentication service, a log of the stationary beacon including the first ephemeral ID.

According to another aspect, a method for monitoring electronic contacts is disclosed. A process may include outputting with the first transceiver of a first smart device, a first ephemeral ID that is not permanently associated with the first smart device but not a first user identifier that is associated with the first smart device, to a second smart device, outputting with a second transceiver of the second smart device, a second ephemeral ID that is not permanently associated with the second smart device but not a second user identifier that is associated with the second smart device, to the first smart device, and outputting with a third transceiver of the first smart device, the first ephemeral ID, the first user identifier and the second ephemeral ID to an authentication service in response to the second ephemeral ID. A technique may include outputting with a fourth transceiver of the second smart device, the second ephemeral ID, the second user identifier, and the first ephemeral ID to the authentication service in response to the first ephemeral ID, and storing in the authentication service an association log comprising first associations between: the first ephemeral ID and the first user identifier, the first ephemeral ID and the second ephemeral ID, and the second ephemeral ID and the second user identifier.

BRIEF DESCRIPTION OF THE DRAWINGS

In order to more fully understand the present invention, reference is made to the accompanying drawings. Understanding that these drawings are not to be considered limitations in the scope of the invention, the presently described embodiments and the presently understood best mode of the invention are described with additional detail through use of the accompanying drawings in which.

DETAILED DESCRIPTION

Figure 1:
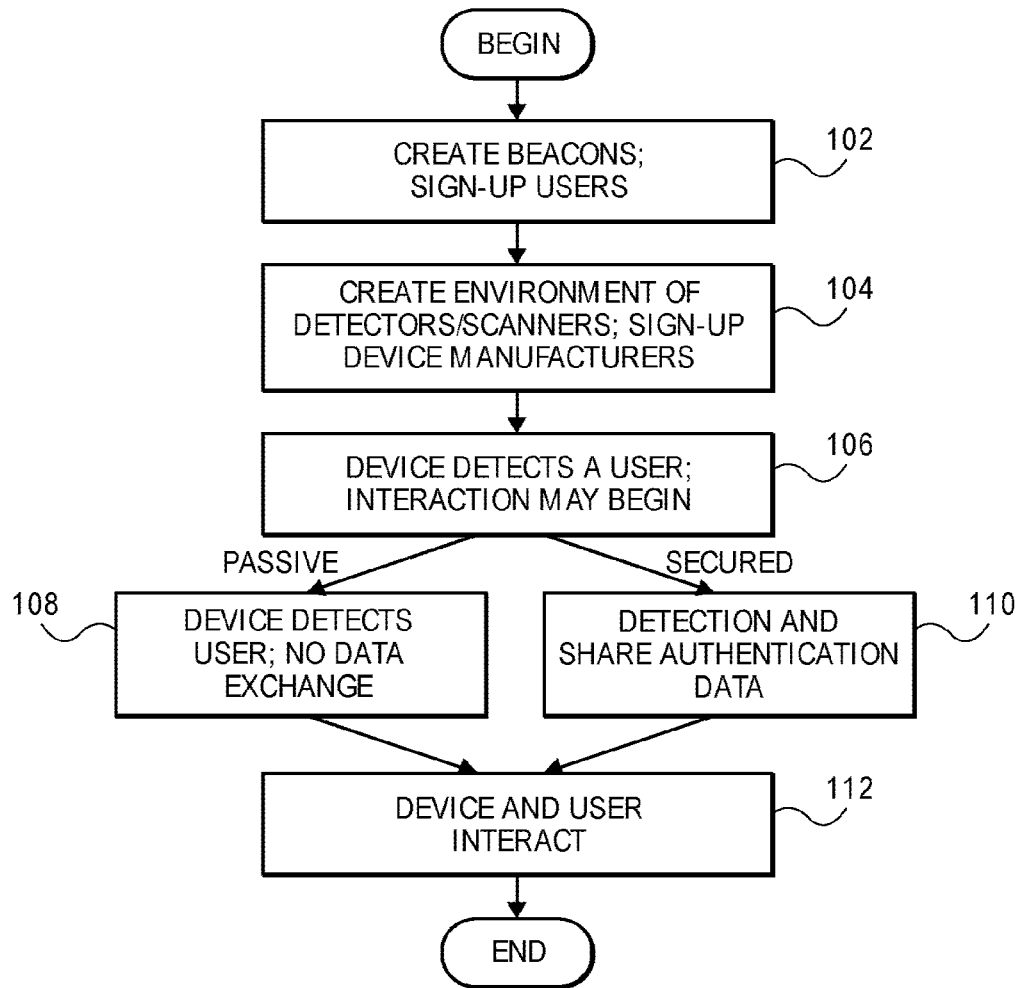
FIG. 1 is an overview flow diagram of a process in accordance with various embodiments.

In the following description, numerous specific details are set forth in order to provide a thorough understanding of the presented concepts. The presented concepts may be practiced without some or all of these specific details. In other instances, well known process operations have not been described in detail so as to not unnecessarily obscure the described concepts. While some concepts will be described in conjunction with the specific embodiments, it will be understood that these embodiments are not intended to be limiting. On the contrary, it is intended to cover alternatives, modifications, and equivalents as may be included within the spirit and scope of the described embodiments as defined by the appended claims.

For example, methods and systems will be described in the context of creating, utilizing, and managing security and authentication for a universal, personal ID signal. In the following description, numerous specific details are set forth in order to provide a thorough understanding of the various embodiments. Particular example embodiments may be implemented without some or all of these specific details. In other instances, well known process operations have not been described in detail in order not to unnecessarily obscure the described embodiments. Various techniques and mechanisms will sometimes be described in singular form for clarity.

It should be noted that some embodiments include multiple iterations of a technique or multiple instantiations of a mechanism or technique unless noted otherwise. For example, a system uses a processor in a variety of contexts. However, it will be appreciated that a system can use multiple processors while remaining within the scope of the described embodiments unless otherwise noted. Furthermore, the techniques and mechanisms will sometimes describe a connection between two entities. It should be noted that a connection between two entities does not necessarily mean a direct, unimpeded connection, as a variety of other entities may reside between the two entities. For example, a processor may be connected to memory, but it will be appreciated that a variety of bridges and controllers may reside between the processor and memory. Consequently, a connection does not necessarily mean a direct, unimpeded connection unless otherwise noted.

Various embodiments describe providing universal identity and physical presence detection in the form of a personal, universal signal. This signal allows a user to interact with devices in the user's environment without having to download vendor-specific apps, set up vendor-specific accounts or be limited to a siloed eco-system of a manufacturer brand. Such a personal universal signal representing an individual allows for devices and software to detect and query the beacon transmitting the signal for information relating to the user and augmented onto the physical environment. This provides a more personalized, efficient, and, in some instances, secure experience for the user.

The embodiments focus on reducing or minimizing user workload to allow for seamless interactions with her environment, such as, for example, the user being able to walk up to a TV anywhere in the world and having the TV (using the user's universal signal) detecting the user and querying for the user's personal preferences and accounts. The user can then, using voice commands, for example telling the TV to play their favorite TV show by saying "play Game of Thrones." The TV, using the user's authenticated universal signal can then access the user's personal preferences and accounts (e.g., Netflix account), and can then pull up the show and play it automatically. This can be done without the user using a specific app on the TV, setting up a TV specific account, logging into accounts, or owning the TV. In another example, a user can walk up to a door, and have the door automatically unlock for the user, once the user reaches a sufficiently close distance so that the user can passively walk through the door without having to do anything. In such examples, this is because the door sensed the user's universal signal ID, verified that the user has access to pass through the door and unlocks the door for the user. Again, this is done without the user being tied to the door manufacturer, or device, or to a specific account or app needed to serve such interaction. As such, the various embodiments provide and enable a universal signal for users and devices to interact, where all parties benefit from a seamless and natural way of interacting in the physical world.

Methods and systems for implementing a smart environment where a user's presence is sensed by a scanner are described in the various figures. In one embodiment, the environment is a physical space in which scanners detect the presence of a user via a universal identifier signal that is emitted from the user's mobile device which operates as a personal beacon. In this framework, the scanners perform most of the back-end operations and, for the beacon (e.g. a user's phone or watch), workload is significantly reduced. In this respect, by taking the burden of implementing the universal ID signal, the environment or physical space providing the framework may be described as intelligent or smart. The users simply need to do move around and behave normally. The devices around them in the space or environment they are moving in detects the users and the smart space performs the necessary communications and processing to realize the benefits described herein.

FIG. 1 is an overview flow diagram of a process in accordance with one embodiment. At step 102 an entity operates as a beacon and moves around in a physical space. In the described embodiment, the entity maybe a human being and the space can be any environment such as a home, an office, a retail store, a lobby, a public space, a sidewalk, to name a few examples. Another way to describe it is that an entity can be any object or thing for which a universal ID signal would be useful, such as a car, bicycle, or animal. At step 104 an environment or space in which at least one scanner operates is created. A scanner can be manifested or implemented in many ways. In the described embodiment, a scanner (also referred to as "device" herein; beacons, typically mobile devices, are referred to herein as "beacon" "user" or "smartphone") can be a home appliance, door lock, monitor, a car, a kiosk, a consumer electronic device, and so on. The type of devices found in an environment or space will naturally be dependent on the nature of the space. At step 104, manufacturers or other entities which either make the scanners or operate or manage them are signed up and registered to have scanners in the environment. A home will have different types of devices than a retail store or an office lobby, and so on. A common feature of most devices or scanners in the described embodiment is that they are generally stationary; they are not expected to move around in the physical space, but they can, and the inventive concepts described herein would still apply. At step 106 a device detects a beacon by virtue of the beacon signal and initial interaction between device and beacon may begin.

The initial interaction may be one of two types. One is referred to as passive interaction shown in step 108. Here the device detects the presence of a beacon signal. The device may not determine the identity of the user, that is, the user remains anonymous. In another passive mode embodiment, the user may be identified but only in a dedicated server operated, typically, by a service provider, described below, and not on the device itself. Although generally this back-end server will be online, in one embodiment the server, that is, the service provider, may be accessible without an Internet connection or being online (e.g., via Ethernet, Zigbee, and the like). This passive scanning or detecting presence of a beacon may be useful in various contexts, such as counting the number of people in a room or space, or whether someone just walked into a space. Essentially, the device wants to sense users around it, but the individual dictates the privacy. The user is the gatekeeper on his or her identity. The device that detects or sense the presence of the user may interact, it may do something, but that action does not have privacy concerns or require user authorization, hence, the passive nature of the interaction.

Another type of interaction that may be initiated is referred to as secured exchange where there is authentication of the user shown in step 110. Here tokens are used to authenticate and the device can make authorization requests. One example that illustrates this clearly is where the device is a door lock which detects the presence of a user and will only unlock if the user is authorized to open the door; the user must prove to the device (door lock) that she has access to open the door. In one embodiment, tokens are used to prove that the user is authorized. The beacon signal has at least one signed token from a back-end server that authenticates the user to the device. Once this authentication is made, the device will perform the relevant action and interact with the user. It may be noted that in either passive or secured exchange scenarios, the device may interact with the user as shown in step 112, but the level or degree of interaction will naturally vary.

Figure 2:
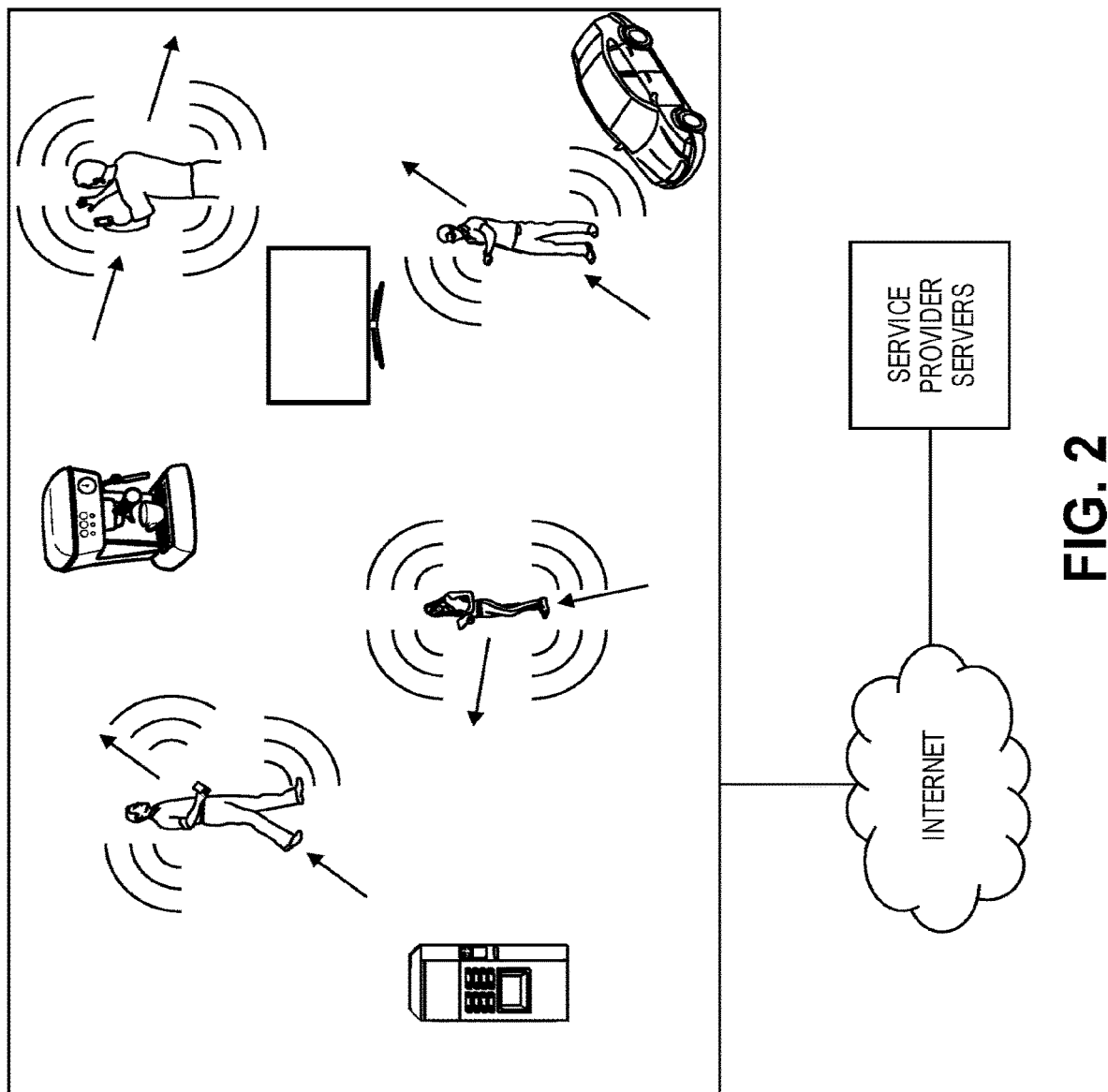
FIG. 2 is an illustration of a physical environment showing different types of devices and users with beacons.

FIG. 2 is an illustration of a physical environment showing different types of devices and users with beacons. Beacons can take various forms, most are Internet-enabled, but the most common are smartphones and wearables, such as watches or bracelets and may include bio-implants and other forms of personal mounted fixtures. As noted, the user will most likely be an individual, but may also be a moving object or an animal, such as a pet. Also shown are devices which can take on many forms, most are Internet-enabled.

Devices may be home appliances and electronics, office equipment, ranging from refrigerators, coffee makers, door locks, TVs, vending machines, kiosks, cars, monitors, and so on. As described in greater detail below, a device may have its own server contained in it (to do universal signal actions) or may not need a service provider server at all. In the described embodiment the device accesses a service provider server to carry out some or all of the operations needed for the present invention. A service provider server, also referred to as the back-end server, is also shown. This server has numerous roles, but one of the primary ones is to authenticate the user and maintain access-control lists for beacons and devices. This back-end server is maintained and operated by the universal ID signal service provider which is responsible for implementing the universal ID signal and smart environment of the present invention. It provides a software module or app (application) that the user installs on her smart phone or wearable thereby enabling it as a personal beacon. And it provides software, hardware or both to device manufacturers and operators. For example, it can provide a software development kit (SDK) for the manufacturer or detector/scanning hardware, such as a Bluetooth module or sensor, if the manufacturer or device operator needs such a hardware component to put in their device. For example, a lock manufacturer may not have the technical means or desire to obtain the appropriate sensor desired for the invention so the service provider can provide the sensor hardware to them and instruct them on how to install it. The device manufacturer will decide what type of capabilities their device(s) will need when interacting with users and what type of security and authorization will be required from its users. It instructs the service provider on what data it needs from the beacon in order to interact securely and safely with its users.

Figure 3:
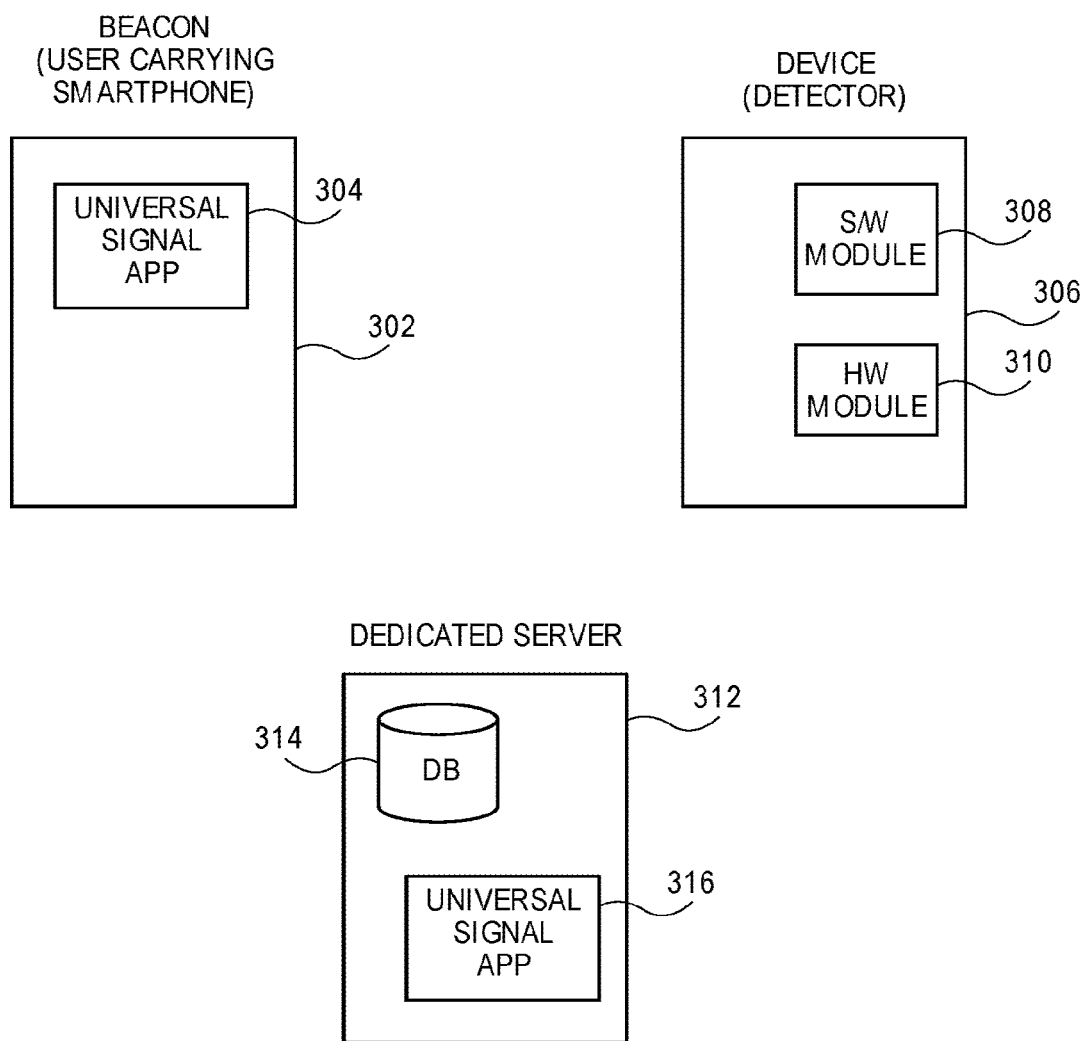
FIG. 3 is a block diagram showing some components for various embodiments of the present invention.

FIG. 3 is a block diagram showing three primary components needed for implementing various embodiments of the present invention. A user acts like a beacon 302. The user, in nearly all instances, a single individual (in some cases a "user" may be a group of people like a family, a group of co-workers, a team, etc.) carries an apparatus that acts as the beacon. As noted, this can be a smartphone, bracelet, watch, or any suitable wearable device. Beacon 302 has installed on it a service provider software module 304, that implements the personal universal ID signal of the present invention.

A device 306 acts as the detector or scanner in the environment. As described, device 306 can take the form of one of a multitude of objects from ranging from appliances to electronic equipment to public vending machines. Nearly all have a software module 308 that is provided by the service provider and installed either by the provider or by the manufacturer. Software module 308, as well as module 304, performs many of the operations described in the flow diagrams below. In some embodiments, device 306 may also have a hardware component 310, such as a Bluetooth component or other hardware needed for connectivity (e.g. transmitter and receiver) with beacon 302 or with a dedicated server, the other component in FIG. 3. This hardware component may be provided by the service provider.

A service provider server 312 is operated and managed by the universal ID signal provider and may have extensive software modules, such as the universal signal app 316, and at least one database 314 which stores data on beacons (users), devices, access control tables, and a wide variety of data needed to implement the universal signal environment of the present invention.

Figure 10:
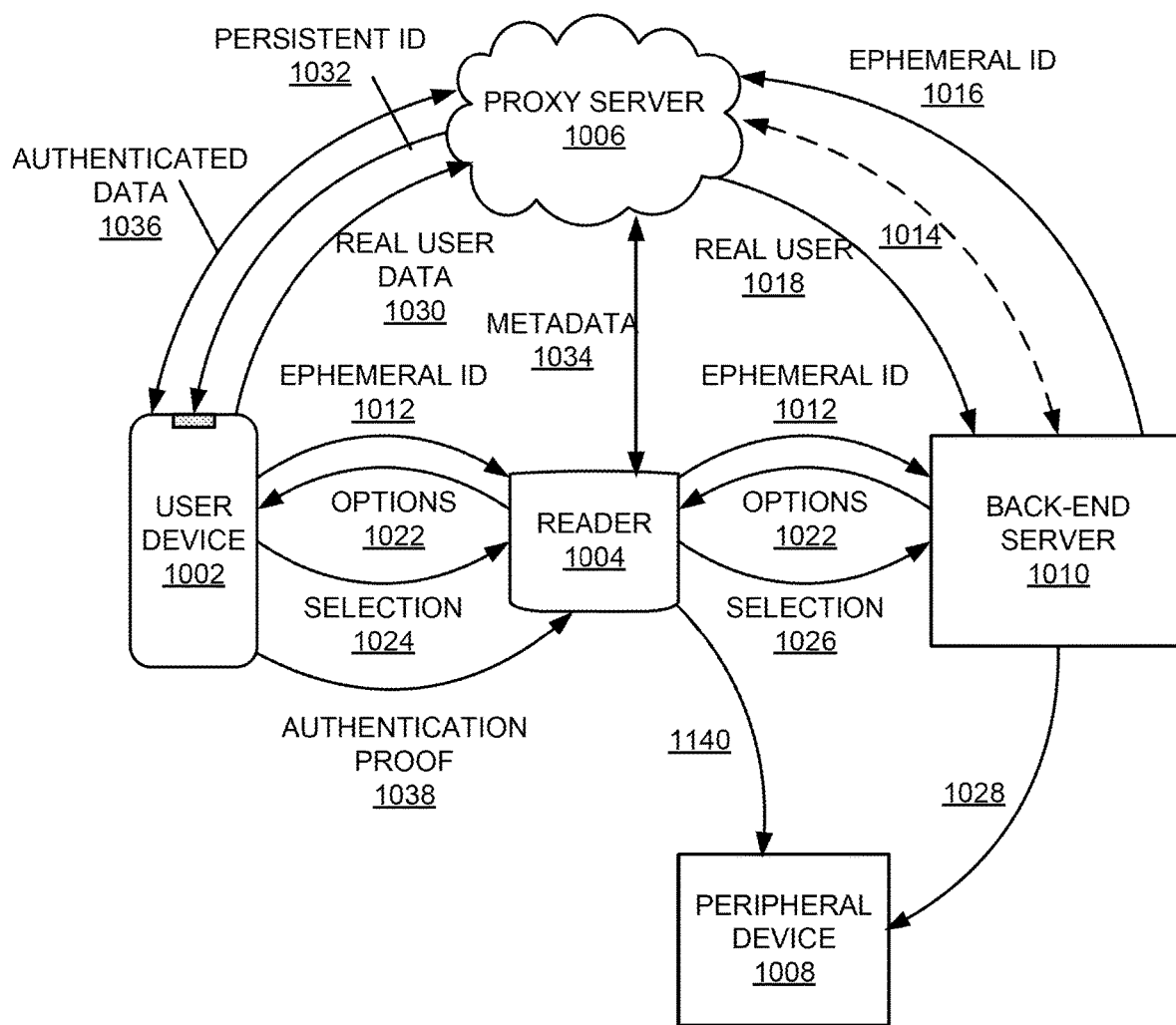
FIG. 10 is a block diagram of a process according to various embodiments of the present invention.

FIG. 10 illustrate a logical flow diagram illustrating the process described below in FIGS. 4A and 4B and FIG. 5. In FIG. 10 systems are illustrated including a user device (e.g. a smart phone, smart watch, ring, tablet, wearable device, augmented reality glasses) 1002 coupled to a reader 1004 and to a cloud-based server 1006, and a peripheral device 1008. In FIG. 10, a peripheral access control system (PACS) 1010 is also illustrated coupled to cloud-based server 1006 and to peripheral device 1008.

Figure 4A:
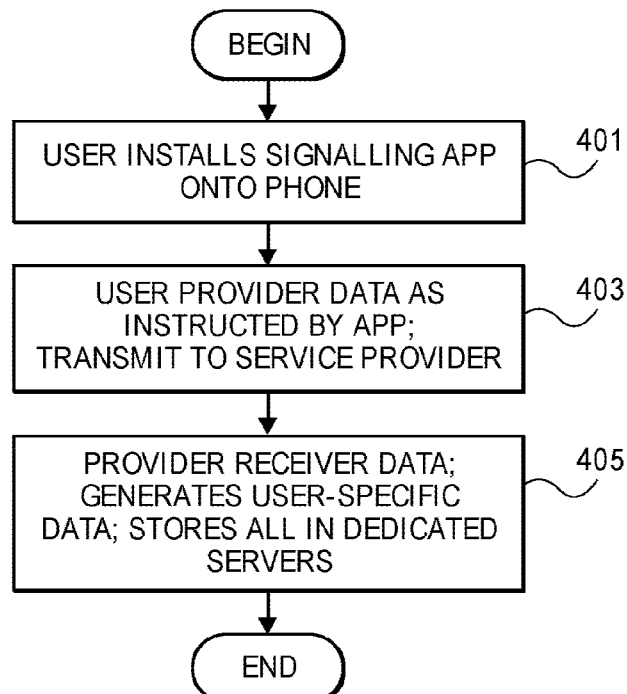
FIG. 4A is a flow diagram of a process of a user joining the universal ID signal framework as implemented by a service provider in accordance with some embodiments.

FIG. 4A is a flow diagram of a process of a user joining the universal ID signal framework as implemented by a service provider in accordance with one embodiment. A user, typically an individual, has decided to join the universal ID signal framework. In one context, an employer may ask all of its employees to join so that the advantages of the universal signal can be realized in an office or company campus environment. The first step taken by the user is shown at step 401 where the user downloads a service provider universal ID signal app ("app") onto her smart phone 1002 or wearable apparatus (for ease of explanation, collectively referred to as "smartphone"). Generally, the app can operate in most widely used personal devices, platforms or operating systems, such as Android, iOS, and others that run on phones, watches, bracelets, tablets, bio-chips and the like. The application may also be termed a security application that runs upon the user's smart device.

Once downloaded and installed, at step 403 the user enters 1030 at least some required basic information about herself. In various embodiments, transmissions between user device 1002 and server 1006 are typically rf communication using WIFI, cellular service (e.g. 4G, 5G, etc.), or the like. Some of the information can be entered at a later time depending on the apparatus that the app is being installed on. In one embodiment, a subset of the data entered by the user results in the creation of various identifiers. One may be referred to generically as a unique ID whose use is limited in that it is used primarily, if not only, by the service provider. This unique ID is not sent to the device, such as an appliance, door lock, coffee machine, etc. Another is a randomly generated identifier, referred to herein as a temporary or ephemeral ID. In some embodiments, the ephemeral ID may include random data, pseudo random data, or data selected from a predetermined set of data. In one embodiment, a portion of the ephemeral ID is provided 1032 to device 1002 and the full ephemeral ID may be generated within user device 1002 based upon the portion of the ephemeral ID from server 1006. In other embodiments, the ephemeral ID may be generated fully within user device 1002 based upon data specified by the app running upon the user device 1002 (e.g. data that identifies to reader 1004 that the ephemeral ID is broadcasted from the app on the user's smartphone. As described above, the ephemeral ID may be combined with random, pseudo random, or data selected from a set of data, or the like ("random"). In some embodiments, ephemeral ID may include at least a first portion including the "random" value and a second portion that includes data that authenticates the ephemeral ID as being authorized by server 1006. In some examples, the authenticating data may be a digitally signed message that reader 1004 may verify itself or with back-end server 1010 and server 1006, a private-key encrypted message that reader 1004 may decrypt itself or via a paired public-key via back-end server 1010 and server 1006, or the like. This ephemeral ID, for example, may be used for anonymous detection by a device of the user. Another identifier created from the user data and provided to 1032 user device 1002 is referred to as a persistent ID, an ID that can be characterized as stable and is created for each user/device manufacturer pair. For example, a user may have different persistent IDs for her relationship with the monitor, another for her relationship with the coffee machine, the car, the door lock, and so on. Each device manufacturer gets a distinct persistent ID for each user (assuming one device from each manufacturer). It may be described as a persistent or permanent version of an ephemeral ID. At step 405 the data entered and created at step 403 is stored in service provider 1006 or manufacture's own dedicated servers 1010, in most cases this will be the service provider servers.

Figure 4B:
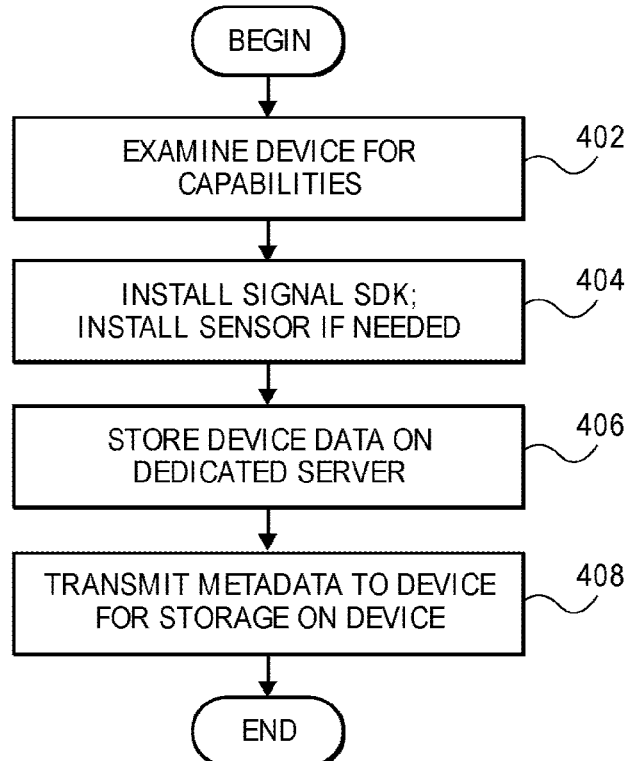
FIG. 4B is a flow diagram of a process of registering and initializing a device so that it can be a universal ID signal sensing device in a physical space in some embodiments.

FIG. 4B is a flow diagram of a process of registering and initializing a device so that it can be a universal ID signal sensing device in a physical space in accordance with one embodiment. At step 402 the service provider determines whether the device has the necessary hardware for being a scanner as needed for implementing the present invention (since the device is new to the space and universal ID framework, the service provider knows that the device does not have the universal ID app yet). The service provider obtains a wide variety of data and metadata about the device, items such as device name, category, location, identifier(s), make, model, time zone and so on. Some of this data is used to let the user know what the device is exactly when she encounters it in a physical real-world space and wants to decide whether to interact with it. However, the threshold question determined at step 402 is whether the device has the right hardware. If it does, the service provider only needs to supply and install universal ID signal software which, in the described embodiment, is in the form of a software development kit (SDK) as shown in step 404. If the device does not have the right hardware for scanning (some smaller scale manufacturers may not have the means or technical skills to include this hardware in their product) the service provider provides one. In this case the software module and the sensor hardware are installed on the device which may be done by the device maker or the service provider.

At step 406 information describing the device is stored by the service provider in a database. This data may be used for enabling interaction between the device 1004 and the beacon 1002. In some scenarios, the data for this interaction may be stored on the device itself wherein the service provider does not play an active role. Some examples of data stored include device ID, single key, private/public key pair, set of commands and interactions, actions the user or device can take, a template which can be customized for different devices. In one embodiment, a template may be described as a pre-defined schema of attributes and metadata. In a simple example, a template for a door lock can have "lock" and "unlock" whereas a template for a car would likely have many more options. At step 408 metadata describing to the device and templates are transmitted 1034 to the device and stored there.

At the end of FIG. 4B, the device is now capable of detecting or sensing a beacon 1002 when a beacon with the universal ID signal app executing on it is in the presence of the device 1004. FIG. 5 is a flow diagram of a process of passive detection of a universal signal presence in accordance with one embodiment. With continued reference to the example in FIG. 10, in FIG. 5, at step 502 a user (as noted, the term "user" is interchangeable with "beacon" and "smartphone" 1002) enters an environment or physical space that has scanning devices, e.g. 1004. It is important to note here that the user is in control of her personal universal ID signal. The user can turn the signal on (by executing the app downloaded at step 401) or not turn it on. There are also measures that can be taken to ensure that the universal signal is coming from the right individual and not an imposter or some other intentional or unintentional unauthorized person. At step 502 the user turns on the signal via a smartphone or wearable apparatus 1002 once another factor has passed. For example, the signal turns on only after a smart watch has detected the user's heart pattern or other biometric means to verify the identity of the user wearing the watch or carrying the smartphone. Only at this point is the signal turned on. This prevents other individuals from impersonating the user by wearing the user's smart watch or other wearable. At step 504 a beacon 1002 in the environment broadcasts 1012 the ephemeral ID. In some embodiments, transmissions between beacon 1002 and reader 1004 may be performed via short-range communications, such as BLE, Zigbee, NFC, or the like. At step 506 a device 1004 detects or senses the beacon 1002 and reads the beacon's ephemeral ID. A non-persistent minimal connection is established initially between the beacon and the device. The universal ID signal app does not tie up the device exclusively (unlike other IoT devices). Because of the non-persistent nature of the connection some typical scaling issues are avoided. No permanent bonding or tie-up is needed in the personal universal ID signal implementation and framework of the present invention.

Steps 502 to 506 describe what can be referred to as a sub-process for ambient sensing of the beacon 1002 by a device 1004. It may be characterized as the simplest use case scenario for the universal ID signal. Ambient sensing can be used in scenarios where users simply have to be distinguished from one another, such as counting how many users are near a device or in a room. This ambient sensing may also be seen as a way for a user to potentially communicate with a device if needed. As illustrated in FIG. 10A, if communication 1014 is possible and the dedicated server, such as a service provider server 1006, can be accessed, the process continues with step 508. In another embodiment, the dedicated server 1006 can be accessed via another communication means, such as Bluetooth, Ethernet, and the like. At step 508, the service provider server 1006 learns private data about the user. It does this by taking 1016 the ephemeral ID or persistent ID and resolving it to a persistent ID or an actual or real user identifier 1018 (as noted, prior to this step, the user was merely an anonymous but distinguishable entity). At step 512 the back-end 1010 receives and verifies permissions attached to the user by examining an access control list. At step 514 the back-end 1010 sends 1022 user data (e.g. options) based on the access control list to the device 1022 via reader 1004, in other words, it sends 1022 to the device 1002 only data about the user that the device 1002 is allowed to see (e.g. options available to the user of device 1002 such as user transaction history, user account status, amount of stored-value remaining, etc.). In some examples, where a peripheral device 1008 is a controlled access point 1008 (e.g. door), an option available may be to unlock or unlatch; where peripheral device 1008 is a television, an option available may be to select from a list of subscription services. In some embodiments, an option may be manually selected by the user on device 1002 and the selection may be sent 1024 to reader 1004, whereas in other embodiments, if there is one option or a default option, the option need not be sent, or the option may automatically be selected by device 1002 and sent back to reader 1004.

In various embodiments, reader 1004 may send 1026 the selected option to back-end 1010, and if authorized, back-end 1010 directs 1028 peripheral device 1008 to perform an action. In the example where peripheral device 1008 is a door, the instruction may be to activate a solenoid, or the like, in a strike plate and allow the user to pull or push open the door; in the example where peripheral device 1008 is a television, the instruction may be to run a Netflix application on the television and to log into Netflix using the users credentials, for example; and the like. In various embodiments, the back-end 1010 stores a matrix of permissions, policies, preferences, and the like regarding users and devices. In one embodiment, it uses the user's persistent ID which, as noted, is particular to that user and a specific device pairing.

In some embodiments, if communication 1014 is not possible in real-time, resolving ephemeral ID may be performed via the transfer of server-authenticated data by smart phone 1002 to reader device 1004, described below, and/or may be performed via the transfer of signed tokens from server 1006 to smart device 1002 described in FIG. 6.

Returning to step 506, if there is no ephemeral ID or the data needed is already on the device, characterized as a "local only" option, the data needed for sensing the beacon 1002 is on the device 1002 itself and user data is requested from the device instead of from a service provider server.

Figure 5:
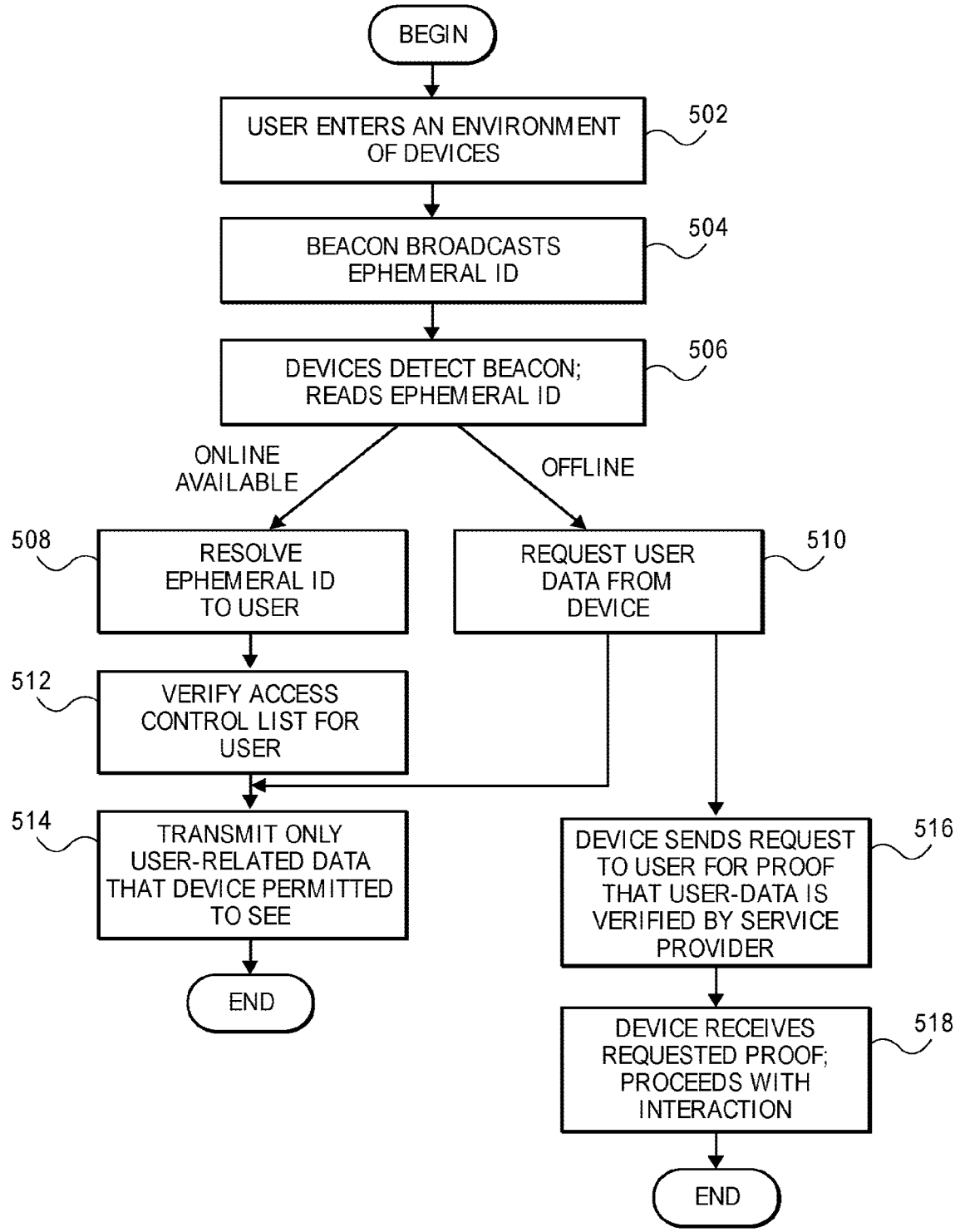
FIG. 5 is a flow diagram of a process of passive detection of a universal signal presence in accordance with some embodiments.

The passive branch shown in FIG. 1 has been described in FIG. 5 steps 502 to 514. Steps 510, 516, and 518 illustrate the secure branch from FIG. 1. As noted, at step 510, in the "local only" step, when the device 1004 (or back-end server 1010) does not access service provider servers 1006 via the Internet, user data is requested from the device. Steps 516 and 518 are needed because the service provider 1006 is not able to authenticate user data (e.g. ephemeral ID or any type of data from the smartphone 1002. The perspective of the queries and actions taken in steps 516 and 518 are from the device 1004 perspective. At step 516 the device 1004 or, more specifically, the universal ID signal software module on the device, needs to be able to verify that data it is receiving from the beacon 1002 at some point has been verified by the service provider 1006 and is still valid. The device 1004 wants to see that the data (the data basically conveying, for instance, "I am John Smith's smartphone") has been vouched for by the back-end server, but that the authentication and identity data the device 1004 receives has been verified. In one embodiment, this is done without using any of the IDs described above (ephemeral, persistent, unique, etc.). Instead data used to verify the identity depends on the scanning device 1004. For example, the data could be an authenticated version 1036 of the user's driver license, or verification of the user's voice or face recognition as matched with a known hash of the user's voice recording or facial image (for example, stored on the user's smartphone) of the user as biometric authentication that the user is the correct, intended user. The authentication may be performed by cloud server 1006, or may be performed by cloud server 1006 in conjunction with a dedicated authentication server. Once the device 1004 receives 1038 this proof or is otherwise confident that the data it is receiving is authentic, control goes to step 518. Here the device receives proof from the smartphone that the user identity data is authentic and that the device 1004 can request performance 1028 of the action by peripheral device 1008 via server 1010, or in alternative embodiments, device 1004 can request 1140 performance of the action directly with peripheral device 1008. As described herein, actions may include unlocking a door, turning a TV on to the user's preferred channel, or make coffee how the user likes it.

Figure 11:
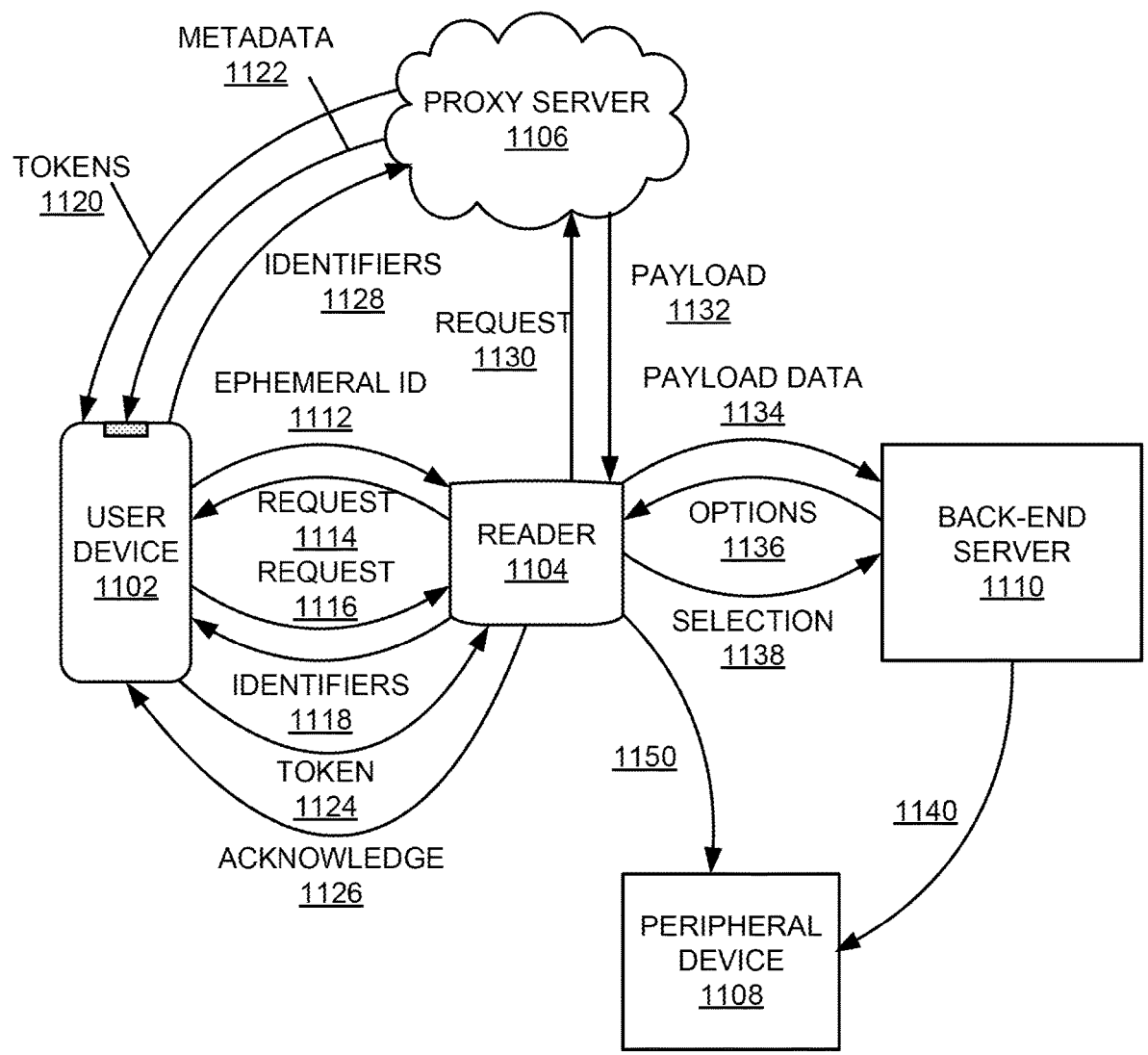
FIG. 11 is another block diagram of a process according to various embodiments of the present invention.

FIG. 11 illustrate a logical flow diagram illustrating the process described below in FIGS. 6-8. In FIG. 11 systems are illustrated including a user device (e.g. a smart phone, smart watch, ring) 1102 coupled to a reader 1104 and to a cloud-based server 1106, and a peripheral device 1108. In FIG. 11, a peripheral access control system (PACS) 1110 is also illustrated coupled to peripheral device 1108.

Figure 6:
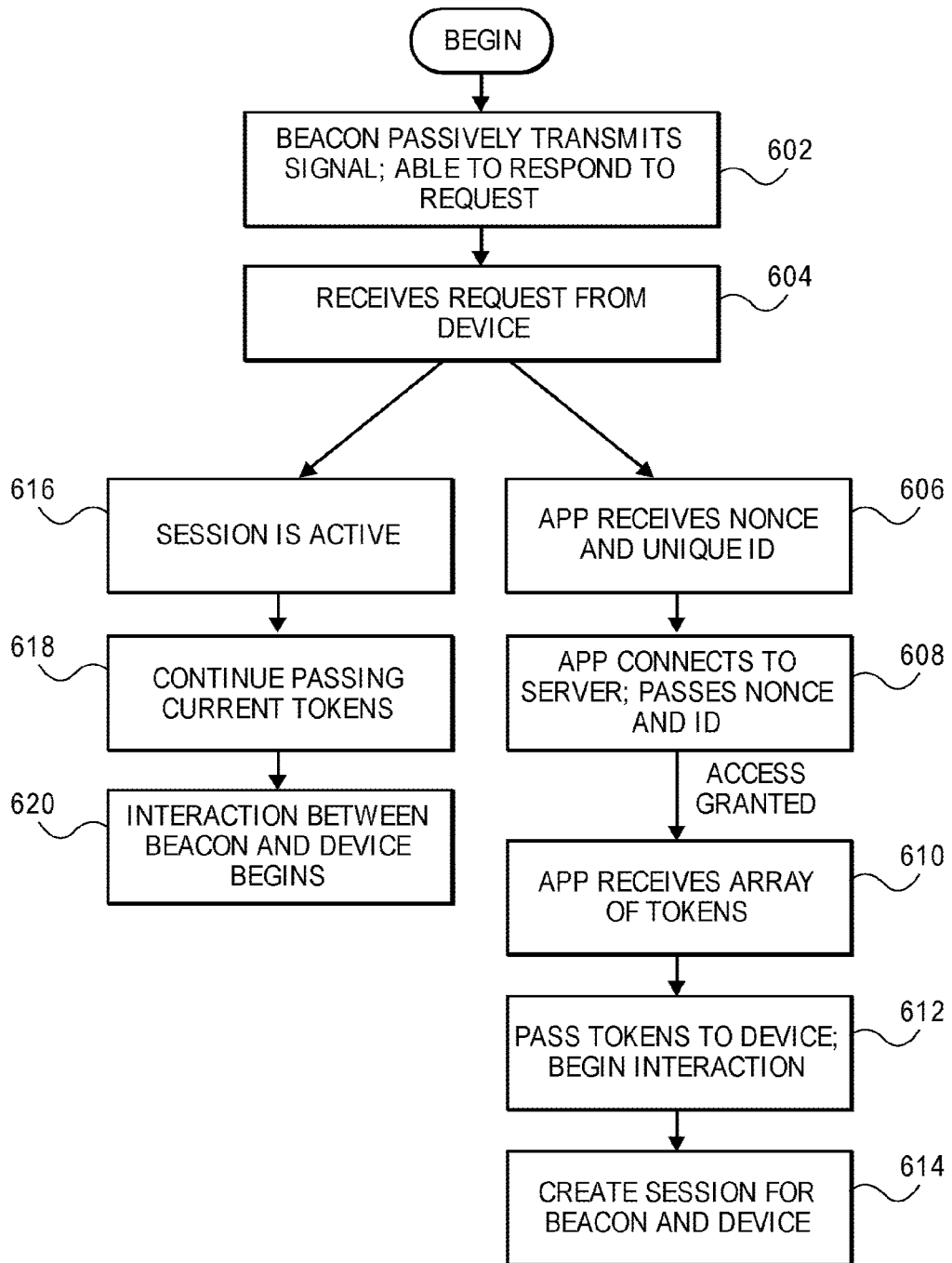
FIG. 6 is a flow diagram of a process of transmitting a universal ID signal between a beacon and a device and initiating interaction between them in accordance with some embodiments.

FIG. 6 is a flow diagram of a process of transmitting a universal ID signal between a beacon 1102 and a device 1104 and initiating interaction between them in accordance with one embodiment. At step 602 the smartphone or wearable 1102 being carried by a user has entered a physical space with universal signal-enabled devices 1104 and is passively transmitting 1112 a universal (ephemeral) ID signal. In some embodiments, transmission 1112 may be performed via short-range communications, such as BLE, Zigbee, NFC, or the like. Similarly. In one embodiment, this is done by the app in the background essentially when the beacon 1102 apparatus is powered on. In other embodiments, the app can be terminated or, in contrast, be in the foreground, and be transmitting a universal, personal ID signal. In various embodiments, reader 1104 may determine whether the ephemeral ID is in the proper format. If not, reader 1104 may ignore it, and if so, reader 1104 may generate a request. In some embodiments, the app is also able to detect a request 1114 from a device 1104 and respond. Although the beacon 1102 has the universal ID signal app from the service provider 1106, it does not need anything from the device 1104 manufacturer in order to receive the request from the device 1104 or respond to it. As noted above, the invention bypasses any form of a "silo" arrangement or framework. The sensors in the devices that are scanning can connect to the beacons.

At step 604 the beacon 1102 receives 1114 a request from the device. The app is able to either recognize the request or not. If it does not recognize the request from the device 1104 or has not seen a request from the device 1104 for a long time (a time exceeding a predetermined threshold), control goes to step 606. In various embodiments, device 1104 may determine whether a session is active based upon identifying information from user device 1102. For example, device 1104 may determine whether portions of the ephemeral ID 1112 are cached within device 1104. The ephemeral ID may be cached by device 1104 in step 614, described below, when a session is initiated.

In some embodiments, if there is no active session, the app requests 1116 a non-repeatable value or nonce from the device and a fixed unique ID for that device. In some embodiments, the nonce may be random data, pseudo random data, or data selected from a predetermined set of data. In other embodiments, this ID can come from the service provider server or through other means, such as through an ID tag via near-field communication or an iBeacon associated with the device. In other embodiments, in response to the transmission 1112 of the ephemeral ID, reader 1104 may provide 1118 the identifiers. At step 606 the app receives 1118 these values. At step 608 the app 1102 connects to the service provider server 1106 and transmits 1128 these two values to the server 1106. In various embodiments, transmissions between user device 1102 and server 1106 are typically rf communication using WIFI, cellular service (e.g. 4G, 5G, etc.), or the like.

In some embodiments, assuming the server 1106 is able to identify the unique ID as belonging to the device 1104, and assuming the user of device 1102 is authorized, server 1106 grants access between the device 1104 and the beacon 1102. The server 1106 uses the nonce for deriving a token as described below. More specifically, it enables access control and security by transmitting 1120 an array of tokens to the smart phone 1102. the server 1106 cannot recognize the device from the ID or determines that there is no interest from the user in accessing or interacting with the device, then tokens are not passed to the smartphone. In some cases, metadata may be passed 1122 to the smartphone which provides publicly available, insecure information related to the device such that the user can act on the information (e.g. options). For example, the device 1104 may be a public device, such as a kiosk or parking meter, and although most of the time the user is likely to ignore the device, if the user wants to learn more about the device (e.g., remaining parking time or rate), the user would be able to do so with the data returned by the dedicated server. In one embodiment, a token has one component that is derived from combining the nonce, the unique device ID, device-specific data, time-limited data, user restrictions, and so on. In one aspect of the present invention that communications between the device 1104 and user 1102 be secure. All the values and factors that go into making the token play a critical role in making the entire universal ID signal framework secure.

The second component of a single token is referred to as a payload section and contains data on user preferences and generally to the user and device. In one embodiment, each token in the array is valid for a limited time period, such as for a few minutes, hours, or days. An array may have a few hundred tokens and can be used to prove validity from a few hours to several days. For example, for commercial building access, a token may last for 4-5 hours and be replenished often to ensure that there are tokens to last the user through the day.

In another embodiment, where access to a service provider server may not be available, tokens can be generated on a device, such as a lock, using other factors, such as biometrics fingerprint, voice recognition, face recognition or retina scanner part of the device, geo-location, expiration time, and so on. These features can also be used even if there is access to the service provider server to provide stronger security. As is known in the art, a token is a signed data item, intended to be used once and discarded (as does an entire array of tokens). Getting back to the importance of security in a universal ID signal framework, the array of tokens that is sent 1120 from the service provider server 1106 to the smart phone 1102, together with other security features, prevents possible hacking and malfeasance, for instance, "replaying" or emulation (harmful devices emulating valid, authorized devices), among others.

At step 612 the app passes 1124 one of the tokens from the array or the entire array of tokens to the device 1104. In some embodiments, the token may pass 1124 via BLE, and in other embodiments, the token may pass via other channel (e.g. NFC, or the like). The device validates the tokens and interactions between the user and the device can begin. More specifically, the universal ID signal software module on the device 1104 validates the tokens and sends 1126 a message to the smart phone stating that they can now communicate. Upon receiving this message, at step 614 the beacon creates a session and the two can now interact. As disclosed above in FIG. 10, the session may include communicating options available, receiving user selections, and the like.

Returning to step 604, if the beacon 1102 app recognizes the request 1114 from the device 1104, control continues with step 616 where a session between the smartphone and the device is already active. As discussed above, determining whether a session is active may be performed based upon cached data within device 1104 (e.g. another token, a MAC address of user device 1102), the ephemeral ID 1112 provided by user device 1102, a challenge and response between device 1104 and user device 1102 based upon a key from a token, or the like. This session may be the same type as the one created at step 614.

The array of tokens may be stored in a cache or local storage on the smartphone. By doing so, the smartphone 1102 does not have to be online; it can be offline and operate fast. At step 618 the smartphone continues passing 1124 tokens to the device. The smartphone keeps the tokens for a predetermined amount of time, a threshold of time that balances security and user convenience, for example, a few hours. After that time has expired, the app on smart phone 1102 gets a new array of tokens from the service provider 1106. If they have not expired, the smartphone can keep using the tokens in the array. At step 620 the interaction between the user 1102 and the device 1104 can resume. In this manner, that is by executing the operations in steps 604 to 614 or steps 604, 616, 618, and 620, a secure, truly universal ID signal that is usable by many different types of devices (from various manufacturers) and users can be implemented.

Figure 7:
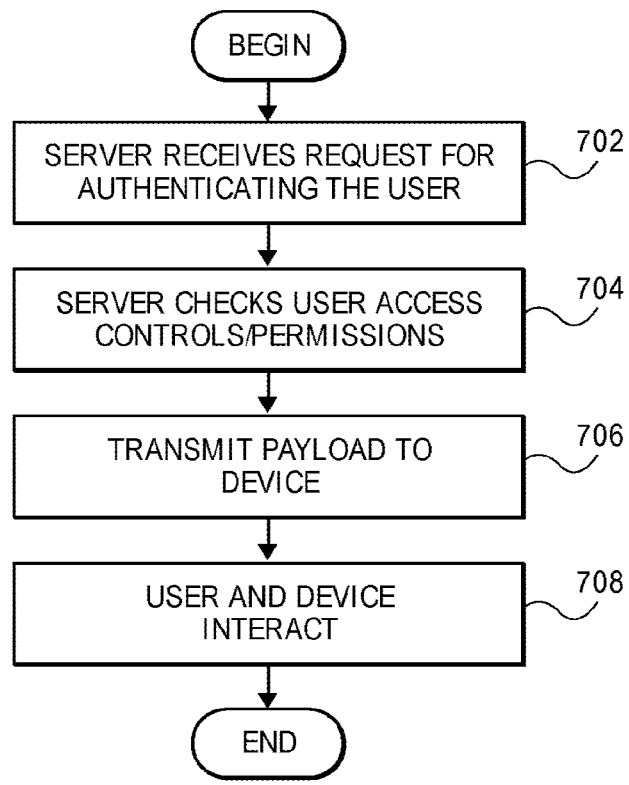
FIG. 7 is a flow diagram of a process of operations that occur on the device when the device is online in accordance with some embodiments.

FIG. 7 is a flow diagram of a process of operations that occur on the device 1104 when the device 1104 is online in accordance with one embodiment. At step 702 the service provider server 1106 receives a request 1130 from a device, for example a car or an appliance, for authenticating a user 1102. It is helpful to note that a device 1104 can only see users who have allowed that specific device to recognize or see them (a category of devices or a specific manufacturer or member group may also be specified). Similarly, in some physical environments, such as a workplace or other secured area, a user is only allowed to see devices that an overseeing entity (e.g., employer) says she is allowed to see or recognize. Such embodiments may be based upon identifiers that are transmitted 1118. If the user device 1102 is not allowed to recognize a reader 1104, based upon the reader's identifiers, the communication may terminate. In other contexts, a device maker may only want users with certain features or characteristics to be able to see or recognize its devices. Various types of scenarios are possible in which either the user or the device maker or owner, manager, and the like can set security protocols regarding who or what can be recognized using the universal ID signal. For example, one benefit of this type of security is that it prevents the equivalent of spamming on both sides. In all scenarios, the underlying security principle that is implemented in the various embodiments of the invention is that either side—user or device— only gets to see and receive what it needs to in order to interact and can only get to that point if the user or device is authorized to see the other. At step 704 the service provider server checks user access controls to see if the user is authorized to use the device and if so what controls or limits are there. There are different techniques or transport mechanisms for how this user access control check can be performed by the service provider. For example, in one embodiment, there may be an out-of-band token exchange or a token server. The common factor is translating the random, non-identifying ID (e.g. ephemeral ID) for the user that was transmitted 1112 initially to the device 1104 into a full set of information about the user. This information can be used in a permission check process. At step 706, assuming the user is authenticated, the service provider server transmits 1132 the payload to the device 1104 so now the device knows the user's preferences, permissions, interaction history, and other information. At step 708 the user 1102 and device 1104 can begin substantive interaction.

Figure 8:
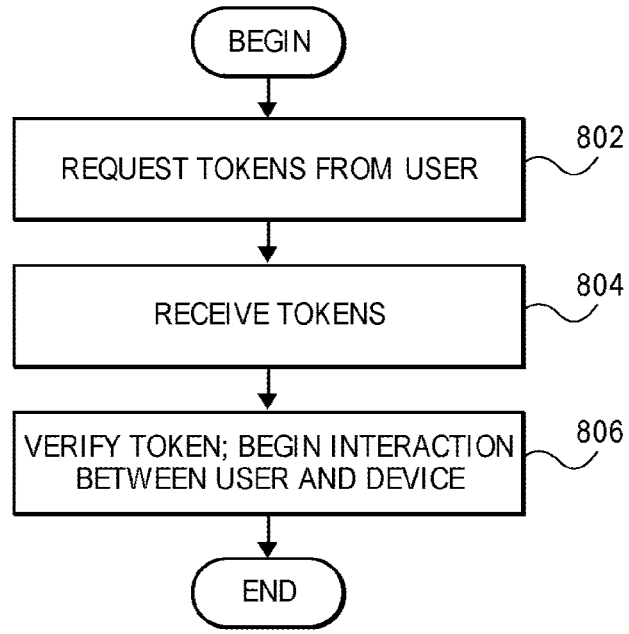
FIG. 8 is a flow diagram of a process that occurs on the device when the device is offline in accordance with some embodiments.

FIG. 8 is a flow diagram of a process that occurs on the device when the device is offline in accordance with one embodiment. The end goal of this process is essentially the same as that of FIG. 7, except here the device 1104 does not communicate with the service provider server 1108. At step 802 the device makes a request 1114 for an array of tokens from the user. The nature and characteristics of this array of tokens are the same as the token array described above. At step 804 the device 1104 receives 1124 a token from the beacon 1102. At step 806 the device 1104 proceeds with verifying the token using only local resources. In various embodiments, it can verify or check the signature in the tokens, it can check to ensure it has not expired or has not been used before. Through these means and others, if available locally, the device authenticates the user and interaction between the user (who may or may not be online) and the offline device can begin. As discussed above, this may include providing 1134 payload data associated with the user and user device 1102, (e.g. a persistent ID, an employee badge number, a store loyalty card, an account number, a stored-value card number, a credit or debit card, telephone number, email address, etc.) that is stored within the token to back-end server 1110.

As noted above, with regard to security, one notable aspect of that is embedded in the validation period of a token. This period can vary from a few minutes to several weeks. A token for a coffee machine may last 20 days whereas for a lock or for making payments, a token may expire after one hour. This security feature is typically set by the device manufacturer; they decide how long to wait before a user has to re-authenticate with the device. Generally, users will have little input in this regard. Another scenario not described in FIGS. 7 and 8 is when the device 1104 and smartphone 1102 are both unable to reach a service provider 1106 or dedicated server and have not connected or interacted with each other before. In this scenario, even though the smartphone has the universal ID signal app and the device registered with the service provider, there is no recognition of each other, let alone any interaction.

In various embodiments, if a back-end server 1110 is used, as described above, options may be provided 1104 to device 1104 and to smart phone 1102, and in response back-end server 110 may receive 1138 a user selection of an option. Back-end server 1110 may then instruct or cause 1140 peripheral device 1108 to perform an action for the user, as discussed above, such as to unlock a door, control a television, provide a product (e.g. a vending machine), etc. In other embodiments, if a back-end server 1110 is not used, device 1104 may directly instruct 1150 peripheral device to perform the action.

Figure 9:
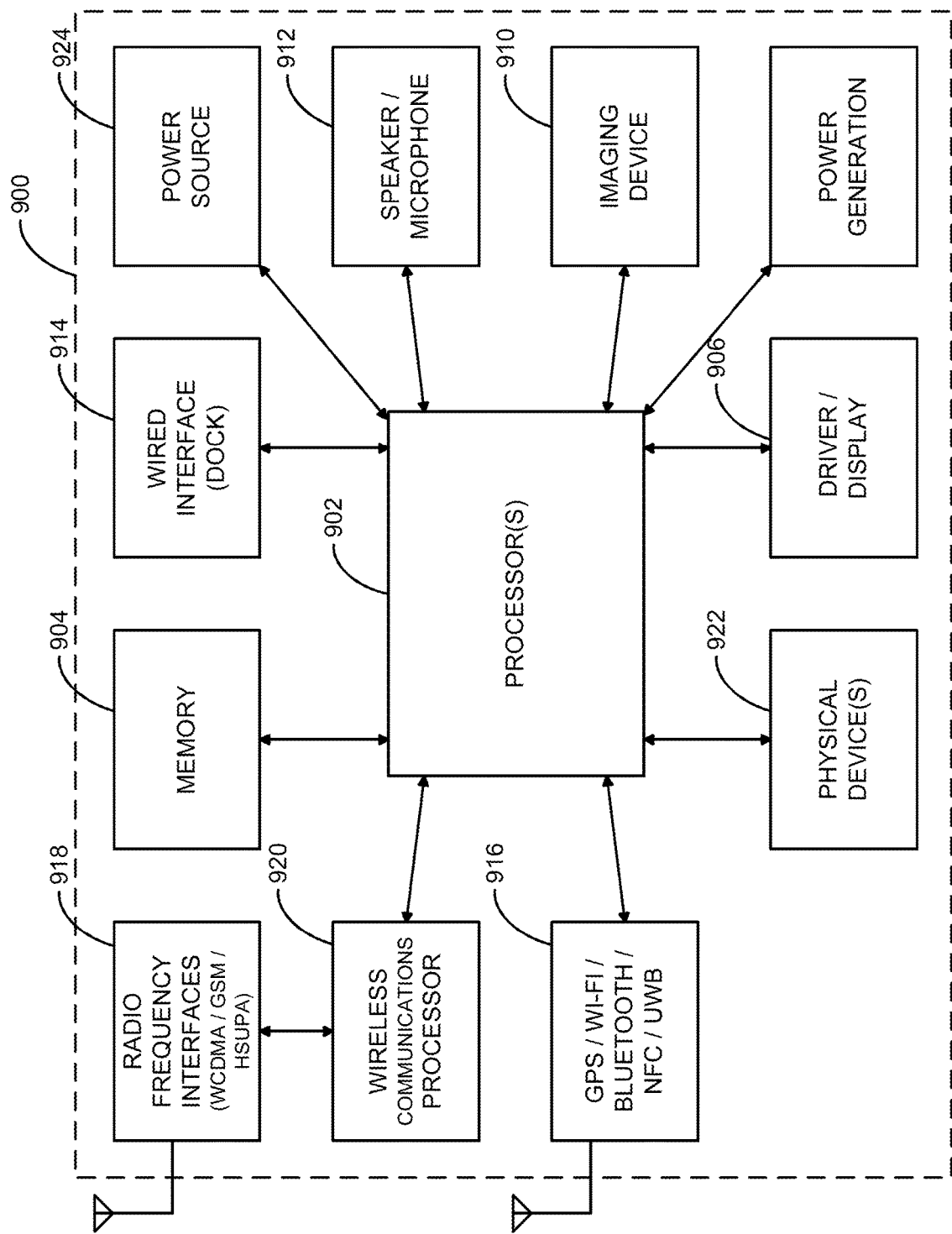
FIG. 9 is a block diagram illustrating an example of a computer system capable of implementing various processes in some embodiments.

FIG. 9 illustrates a functional block diagram of various embodiments of the present invention. More specifically, it is contemplated that from user smart devices to cloud-based servers may be implemented with a subset or superset of the below illustrated components. In FIG. 9, a computing device 900 typically includes an applications processor 902, memory 904, a display 906, an image acquisition device 910, audio input/output devices 912, and the like. Additional communications from and to computing device 900 can be provided by via a wired interface 914 (e.g. dock, plug); a GPS/Wi-Fi/Bluetooth interface/UWB 916; RF interfaces 918 and driver 920, and the like. Also included in some embodiments are physical sensors 922 (e.g. (MEMS-based) accelerometers, gyros, magnetometers, pressure sensors, temperature sensors, bioimaging sensors etc.).

In various embodiments, computing device 900 may be a hand-held computing device (e.g. Apple iPad, Microsoft Surface, Samsung Galaxy Note, an Android Tablet); a smart phone (e.g. Apple iPhone, Google Pixel, Samsung Galaxy S); a portable computer (e.g. netbook, laptop, convertible), a media player (e.g. Apple iPod); a reading device (e.g. Amazon Kindle); a fitness tracker (e.g. Fitbit, Apple Watch, Garmin or the like); a headset or glasses (e.g. Oculus Rift, HTC Vive, Sony PlaystationVR, Magic Leap, Microsoft HoloLens); a wearable device (e.g. Motiv smart ring, smart headphones); an implanted device (e.g. smart device medical) or the like. Typically, computing device 900 may include one or more processors 902. Such processors 902 may also be termed application processors, and may include a processor core, a video/graphics core, and other cores. Processors 902 may include processor from Apple (A12, A13), NVidia (Tegra), Intel (Core), Qualcomm (Snapdragon), Samsung (Exynos), ARM (Cortex), MIPS technology. In some embodiments, processing accelerators may also be included, e.g. an AI accelerator, Google (Tensor processing unit), a GPU, or the like. It is contemplated that other existing and/or later-developed processors may be used in various embodiments of the present invention.

In various embodiments, memory 904 may include different types of memory (including memory controllers), such as flash memory (e.g. NOR, NAND), SRAM, DDR SDRAM, or the like. Memory 904 may be fixed within computing device 900 and may include removable (e.g. SD, SDHC, MMC, MINI SD, MICRO SD, CF, SIM). The above are examples of computer readable tangible media that may be used to store embodiments of the present invention, such as computer-executable software code (e.g. firmware, application programs), security applications, application data, operating system data, databases or the like. It is contemplated that other existing and/or later-developed memory and memory technology may be used in various embodiments of the present invention.

In various embodiments, display 906 may be based upon a variety of later-developed or current display technology, including LED or OLED status lights; touch screen technology (e.g. resistive displays, capacitive displays, optical sensor displays, electromagnetic resonance, or the like); and the like. Additionally, display 906 may include single touch or multiple-touch sensing capability. Any later-developed or conventional output display technology may be used for the output display, such as LED IPS, OLED, Plasma, electronic ink (e.g. electrophoretic, electrowetting, interferometric modulating), or the like. In various embodiments, the resolution of such displays and the resolution of such touch sensors may be set based upon engineering or non-engineering factors (e.g. sales, marketing). In some embodiments, display 906 may integrated into computing device 900 or may be separate.

In some embodiments of the present invention, acquisition device 910 may include one or more sensors, drivers, lenses and the like. The sensors may be visible light, infrared, and/or UV sensitive sensors that are based upon any later-developed or convention sensor technology, such as CMOS, CCD, or the like. In some embodiments of the present invention, image recognition algorithms, image processing algorithms or other software programs for operation upon processor 902, to process the image data. For example, such software may pair with enabled hardware to provide functionality such as: facial recognition (e.g. Face ID, head tracking, camera parameter control, or the like); fingerprint capture/analysis; blood vessel capture/analysis; iris scanning capture/analysis; otoacoustic emission (OAE) profiling and matching; and the like. In various embodiments of the present invention, imaging device 910 may provide user input data in the form of a selfie, biometric data, or the like.

In various embodiments, audio input/output 912 may include conventional microphone(s)/speakers. In various embodiments, voice processing and/or recognition software may be provided to applications processor 902 to enable the user to operate computing device 900 by stating voice commands. In various embodiments of the present invention, audio input 912 may provide user input data in the form of a spoken word or phrase, or the like, as described above. In some embodiments, audio input/output 912 may be integrated into computing device 900 or may be separate.

In various embodiments, wired interface 914 may be used to provide data transfers between computing device 900 and an external source, such as a computer, a remote server, a storage network, another computing device 900, a client device, or the like. Embodiments may include any later-developed or conventional physical interface/protocol, such as: USB, micro USB, mini USB, USB-C, Firewire, Apple Lightning connector, Ethernet, POTS, custom dock, or the like. In some embodiments, wired interface 914 may also provide electrical power, or the like to power source 924, or the like. In other embodiments interface 914 may utilize close physical contact of device 900 to a dock for transfer of data, magnetic power, heat energy, light energy, laser energy or the like. Additionally, software that enables communications over such networks is typically provided.

In various embodiments, a wireless interface 916 may also be provided to provide wireless data transfers between computing device 900 and external sources, such as computers, storage networks, headphones, microphones, cameras, or the like. As illustrated in FIG. 9, wireless protocols may include Wi-Fi (e.g. IEEE 802.11 a/b/g/n, WiMAX), Bluetooth, Bluetooth Low Energy (BLE) IR, near field communication (NFC), ZigBee, Ultra-Wide Band (UWB), Wi-Fi, mesh communications, and the like. As described above, data transmissions between computing device 900 and identity reader 1104 may occur via UWB, Bluetooth, ZigBee, Wi-Fi, a mesh network, or the like.

GPS receiving capability may also be included in various embodiments of the present invention. As illustrated in FIG. 9, GPS functionality is included as part of wireless interface 916 merely for sake of convenience, although in implementation, such functionality may be performed by circuitry that is distinct from the Wi-Fi circuitry, the Bluetooth circuitry, and the like. In various embodiments of the present invention, GPS receiving hardware may provide user input data in the form of current GPS coordinates, or the like, as described above.

Additional wireless communications may be provided via RF interfaces 918 and drivers 920 in various embodiments. In various embodiments, RF interfaces 918 may support any future-developed or conventional radio frequency communications protocol, such as CDMA-based protocols (e.g. WCDMA), GSM-based protocols, HSUPA-based protocols, G4, G5, or the like. In the embodiments illustrated, driver 920 is illustrated as being distinct from applications processor 902 and wireless interface 916. However, in some embodiments, various functionality are provided upon a single IC package, for example the Marvel PXA330 processor, and the like. It is contemplated that some embodiments of computing device 900 need not include the wide area RF functionality provided by RF interface 918 and driver 920.

In various embodiments, any number of future developed, current operating systems, or custom operating systems may be supported, such as iPhone OS (e.g. iOS), Google Android, Linux, Windows, MacOS, or the like. In various embodiments of the present invention, the operating system may be a multi-threaded multi-tasking operating system. Accordingly, inputs and/or outputs from and to display 906 and inputs/or outputs to physical sensors 922 may be processed in parallel processing threads. In other embodiments, such events or outputs may be processed serially, or the like. Inputs and outputs from other functional blocks may also be processed in parallel or serially, in other embodiments of the present invention, such as acquisition device 910 and physical sensors 922.

In some embodiments of the present invention, physical sensors 922 (e.g. MEMS-based) accelerometers, gyros, magnetometers, pressure sensors, temperature sensors, imaging sensors (e.g. blood oxygen, heartbeat, blood vessel, iris data, etc.), thermometer, otoacoustic emission (OAE) testing hardware, and the like may be provided. The data from such sensors may be used to capture data associated with device 900, and a user of device 900. Such data may include physical motion data, pressure data, orientation data, or the like. Data captured by sensors 922 may be processed by software running upon processor 902 to determine characteristics of the user, e.g. gait, gesture performance data, or the like. In some embodiments, sensors 922 may also include physical output data, e.g. vibrations, pressures, and the like.

In some embodiments, a power supply 924 may be implemented with a battery (e.g. LiPo), ultracapacitor, or the like, that provides operating electrical power to device 900. In various embodiments, any number of power generation techniques may be utilized to supplement or even replace power supply 924, such as solar power, liquid metal power generation, thermoelectric engines, rf harvesting (e.g. NFC) or the like.

FIG. 9 is representative of one computing device 900 capable of embodying the present invention. It will be readily apparent to one of ordinary skill in the art that many other hardware and software configurations are suitable for use with the present invention. Embodiments of the present invention may include at least some but need not include all of the functional blocks illustrated in FIG. 9. For example, a smart phone configured to perform may of the functions described above includes most if not all of the illustrated functionality. As another example, a biometric acquisition device, e.g. a smart ring (electronic devices enclosed in a ring-shaped shell, enclosure, or form factor), may include some of the functional blocks in FIG. 9, it need not include a high-resolution display 930 or a touch screen, a speaker/microphone 960, wired interfaces 970, or the like. In still other examples, a cloud-based server or a virtual machine (VM) may not include image acquisition device 912, MEMs devices 922, GPS capability 916, and the like, further components described above may be distributed among multiple computers, virtual machines, or the like.

Figure 12:
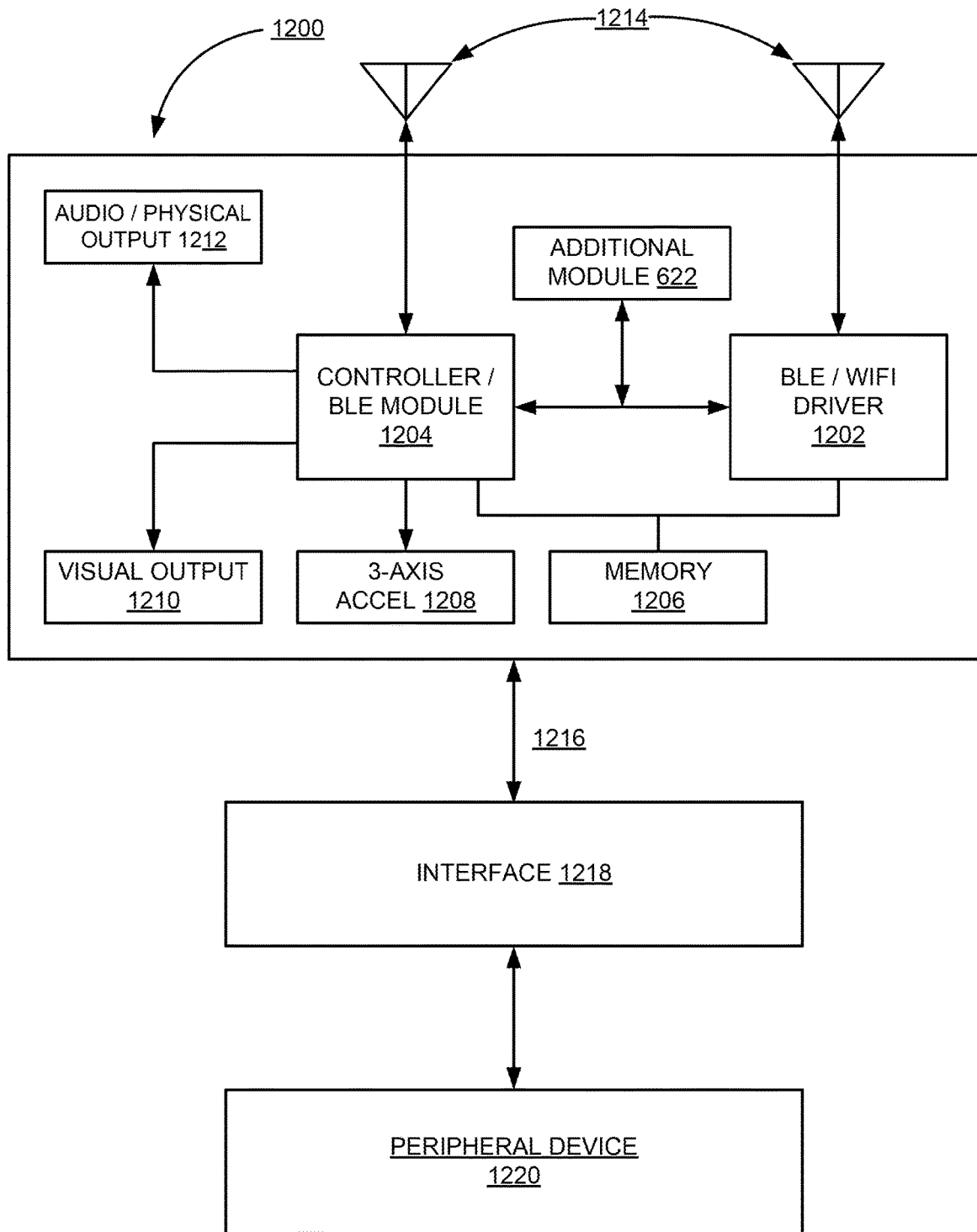
FIG. 12 is another block diagram of a reader according to various embodiments of the present invention.

FIG. 12 illustrates a block diagram according to some embodiments of the present invention. More specifically, FIG. 12 illustrates a block diagram of a reader device 1200 described herein and illustrated as reader 1104 and 1104 in FIGS. 11 and 12. In some embodiments, device 1200 includes an rf control module 1202, a controller 1204, memory 1206, an accelerometer 1208, visual/haptic output 1210, audio output 1212, antennas 1214, interface bus 1216, and an interface module 1218.

In some embodiments, controller 1204 may be embodied as a Nordic nRF52832 system on a chip, suitable for controlling Bluetooth low energy (BLE) communications and for performing various functionalities described herein. Controller 1204 may include a processor, such as a 32-bit ARM® Cortex®-M4F CPU and include 512 kB to 124 kB RAM. In various embodiments, other types of SoC controllers may also be used, such as Blue Gecko from Silicon Labs, CC2508 from TI, or the like. Controller 1202 may be embodied as a muRata 1LD Wi-Fi/BLE module, suitable for controlling Bluetooth low energy (BLE) and Wi-Fi communications. Controller 1202 may include a processor, such as a 32-bit ARM® Cortex®-M4. In various embodiments, other types of controllers may also be used, such as CYW43012 from Cypress, or the like. In some embodiments, modules 1202 and 1204 enable communication via short range communications protocols, such as BLE, Zigbee, or the like. Modules 1202 and 1204 may also support mesh networking via BLE, Wi-Fi 12, or the like. In some embodiments, module 1202 also supports Wi-Fi communications to communicate over a wide-area network (e.g. Internet).

In various embodiments, memory 1206 may include non-volatile memory storing embodiments of the executable software code described herein. In some embodiments, the memory may be SRAM, Flash memory, or the like. In FIG. 12, audio/haptic output 1212 is provided to give a visitor with audio feedback or haptic feedback and visual output 1202 is provided to give a visitor visual feedback in response to the visitor approaching reader device 1200. In some embodiments, visual output 1202 may be one or more LED lights having different colored outputs, may be a status display panel. The feedback may be provided to the visitor based upon the visitor's security application running upon the smart device and interacting with reader device 1200. For example, if the smart device does not have the proper credentials for reader device 1200, a harsh buzzing sound may be played by audio output 1210, and a red flashing light may be output by visual output 1210; if the smart device is authenticated with reader device 1200, a bell ding sound may be played and the text "OK" may be displayed on a display; if the smart device is not authenticated with reader device 1200, an audio message and textual message may be output: "Not authenticated. For access, please call" or the like.

Accelerometer 1228 is provided in some embodiments to determine whether reader device 1200 is tampered with. For example, after installed and operable on a mounting location (e.g. on a wall), accelerometer 1228 monitors the orientation of accelerometer 1228 with respect to gravity. If a party attempts to remove reader device 1200 from a mounting surface, accelerometer 1228 will be able to sense the change in orientation. Based upon the change in orientation exceeding a threshold, a number of actions may be taken by reader device 1200. One action may be to cease operation of reader device 1200, another action may be to alert a remote server of the tampering, and the like. In other embodiments, other physical sensors, e.g. pressure sensors, light sensors, gyroscopes, and the like may be used. Such embodiments may also provide tamper detection indication.

In FIG. 12, interface 1216 is used to couple reader device 1200 to interface module 1218. In various embodiments, interface module 1218 interfaces with any number of external functional modules. In one configuration, an external functional module 1220 may be a peripheral device under control, e.g. an electronically controlled door latch, a television, a vending machine, a computer, an electronic panel, an automobile, a kiosk or the like; in another configuration, external functional module 1220 may be an existing module that is configured to read conventional low frequency or high frequency (LF/HF/UHF/etc.) based proximity cards or badges; and the like. In some embodiments, external reader module 1220 may be an existing reader mounted upon a wall, or the like. In some embodiments, interface 1216 may provide power to reader module 1200, interface 1216 may transmit data from reader device 1200 to interface module 1218 (e.g. credentials), provide power or the like.

In one configuration, rf control module 1202 is not used, and only one BLE antenna 1214 is provided; in another configuration, modules 1202 and 1204 are both used, and two BLE antennas 1214 are used (one specifically for scanning for ephemeral IDs within a geographic region and one specifically for handling communications with a smart device). Such embodiments are particularly useful in high volume situations wherein one BLE antenna may receive ephemeral IDs from many different smart devices (e.g. 12 users walking down a hall near a security door or vending machine), whereas the other BLE antenna will provide the credentials and receive tokens from the specific users' smart phones who want to interact with the reader (e.g. to enter the security door, to receive a good, to access a computer or the like). In other embodiments, other channels may be used to provide the above communications, such as short-range Wi-Fi, Zigbee, NFC, ANT, or the like.

In still another configuration, additional modules 1222 may be provided to add additional functionality to reader module 1200. In some embodiments, module 1222 may be an rf encoding module that converts data associated with the user (e.g. a badge number) into a format (e.g. LF/HF/UHF badge or tag) that is readable by a conventional RFID card or badge reader. In some embodiments, module 1222 may include one or biometric capture devices that capture biometric data of a user associated with a smart device. In some embodiments, biometric data may include facial data, voice data, eye data (e.g. iris, retina, blood vessel), print data (e.g. fingerprints, palm print, blood vessel), movement data (e.g. signature, movement, gait), and the like that may be used to facilitate authentication of the visitor.

In one embodiment systems and methods are provided for universal presence detection and interactions. As a non-limiting example, the universal ID signal is created that represents clients, people or other objects hereafter "first party" where any system, sensor or software can detect that signal and queries it for relevant information for serving the person or object. As a non-limiting example this entails a method of turning mobile devices, wearables or biochips and the like hereafter "device" into a personal transponder (e.g. transceiver) that emits a unique signal via Bluetooth low energy as in one instance to represent the presence of the person, e.g., user. Things around the user can detect the signal and can transform the signal into a meaningful metadata that represents the person or object of the signal.

In one embodiment systems and methods are provided for instant execution of actions through wireless connections. As a non-limiting example this incorporates a peripheral and central mode of operation is used to obtain a token. The token is only executed when it is within a threshold to make for an instant action. By scanning the address or other identifier of the device, and keeping a token cached locally in the embedded system, the embedded system can then act instantly on any command/intent that the mobile client triggers such that there is no lag between the intent and the performed action.

In one embodiment systems and methods are provided for sensing the presence of identifiable objects. As a non-limiting sensor technology is used that scans and primes objects nearby which emits a unique universal ID signal. As a non-limiting example, the sensor can trigger an emitter to provide specific information about it or the emitter of the presence universal ID signal can detect the scanner and do the same. In this embodiment systems and methods are provided of turning a sensor into both a peripheral and central device for the purposes of detecting the presence of objects nearby. This can be used to securely make the handshake and reduce the load on the first party by using the scanner on the sensor to do most of the hard work to not overload the peripheral modes.

In another embodiment systems and methods are provided for passive detection and identification of passengers, first party, on a moving vehicle. As a non-limiting example this can include use of an accelerometer and a signaling protocol to conclude that the object being sensed is in fact travelling with the vehicle that the sensor is attached to. Steps are taken with the universal ID signal and shares commands between the sensor the passenger to trigger a confirmation that the passenger is travelling on the vehicle. The main use case is to sense when people are travelling on a bus or train and to be able to do things such as process payments for the traveler automatically or to track the passenger's route.

In another embodiment systems and methods are provided to secure offline interactions. As a non-limiting example, a method is provided for collecting a plurality of commands on the first party and a bloom filter is used on the sensor side to certify a secure command through BLE (Bluetooth low energy) has happened without any fall back over the internet. As a non-limiting example this method can be used to issue any type of command, including but not limited to payments, metadata, and the like, between things and a sensor with limited storage capacity within proximity without the need for an internet connection.

In another embodiment systems and methods are provided for secure physical payment processing over wireless local networks. As a non-limiting example, a method of handshaking the connection to a POS/terminal and the first party's mobile device is used where both sides are securely verified. Once an amount is entered in a terminal and applied to the detected entity the payment is batched and processed on the back end. In this manner there is no exchange of payment information between the terminal and the first party for a safer and secure payment process. In this embodiment the system defines that things are done in a unique way for anything which as non-limiting examples can be Google Hand's Free, Apple Pay and the like.

In one embodiment systems and methods are provided for wireless identification for connecting second party account services access via a proxy agent. As non-limiting examples the system and method allow devices to detect the first party and access first party accounts including but not limited to: Andorra, Netflix, one or more Calendars, an Amazon Account, and the like, through a proxy agent. As a non-limiting use case is the ability to walk up to any Echo like device and it instantly recognizes and can say "Hello first party X" and first party X can say to it "play my easy music station on Pandora", having never used the device before or having to set up first party X's specific account with the Echo device. This is an improvement over the need to set up an account and limit these devices to just the users with accounts set to them. Another use case is the ability to use any TV Screen and X's avatar shows. As non-limiting examples as first party X taps it all of its' Netflix shows, YouTube videos, and the like, show up for first party X and to instantly play it. As first party X walks away it all disappears. All of this exposes an oath to the Netflix account of first party X to the TV software to start playing it without forcing first party X to do another separated Netflix login on the TV.

In another embodiment systems and methods are provided for wireless identification of fixed and roaming objects. As a non-limiting example objects are discovered wirelessly. As non-limiting examples this can be achieved by using this to cover the use case of being able to create a wireless (barcode like identifier) that every device can emit to be identified, including but not limited to, the VIN of a car, a serial number of a customer electronic, and the like. This identification can then be used for situations such as auto paying for parking meters and parking and getting access to buildings, and the like. As another non-limiting example this can be used for turning people into beacons. In this manner each individual object then has its own identity beacon.

In another embodiment systems and methods are used for bi-directional communicating beacons. As a non-limiting example this can be one of a bi-directional beacon that can not only emit an advertising packet but can also scan for advertisements to query things around it for useful information or metadata that can be used to serve the subject. The limitation of beacons is that they all require a corresponding app that listening for the specific beacon to be of any use. By creating a bi-directional beacon, it can serve people that have the apps. It can also serve people who do not have the apps but detects their presence signature to serve them. This provides a self-contained beacon device similar to current beacons, that operates in both peripheral and central modes for the bi-direction natures of detection and communications.

In another embodiment systems and methods are provided for a wireless digital driver's license and verified identification. As a non-limiting example, this creates an electronic driver's license that emits as a wireless signal. Police authorities and the like can detect and instantly query the license by standing next to the first party. The first party never needs to carry a license anymore or present any info and their privacy is intact with the use of a universal ID signal. As non-limiting examples this provides how the first party enters its information into its account, how identification is verified through several methods, as well as how an associated universal ID signal provides for security to make the universal ID signal securely available to authorities through their own mobile devices.

In another embodiment systems and methods are provided for automatically paying fares on public transport. As a non-limiting example provides for, (i) automatically detecting passengers who are on a public transport vehicle, (ii) detects when they get on and off and (iii) processes payment for the fare automatically for them on the back end without the user having to do anything.

In another embodiment systems and methods are provided for secure decentralized wireless identification. As a non-limiting example this provides for the use of a first party's fingerprint, voice, appearance, and the like to verify identity to some other system without sharing the information with second party systems. In one embodiment this is achieved by using the app of the present invention on a device, including but not limited to a mobile device, as the primary validator. A presence protocol is used to bounce the verification step between the proxy detector (fingerprint/scanner, voice/mic, appearance/camera) and the first party's proxy app such that the first party's identity and bio-info stays within the first party's control and is never shared with any central server or second party system. This provide a secure decentralized method of identification without the need to share first party information with others. This can be used for high security needs. It can also be used for additional situations including but not limited to: buying a new device and using the first party's fingerprint to log in and create an account with the device service provider without the need to fill out any form. The device instantly knows the first party name and says:

"Hello first party X, I'm your new radio, how are you today?". As non-limiting examples this includes but is not limited to:

Vision—face detected and checking that its first patty X by hashing matching with the face first party X has on its device;

Voice—voice detected and checking that it's the first party by hashing its voice and checking with the proxy app to verify it is the first party;

Fingerprints; and

Other Biometrics.

All never leaving the first party's device.

In another embodiment systems and methods are provided for a universal people sensor microchip for universal sensing and identifying people interacting with a product or service. As a non-limiting example this can include a "Universal People Sensor" as a stand-alone dedicated microchip designed to be embeddable in any consumer electronic or manufactured product to allow the product detect people that are using the product. It can also be used to extract information from the person, all without the person downloading a specific app or the device creating its own sensor. As a non-limiting example this provides a method to create the sensor, and how the sensor does what it does to identify and extract data from first parties. In one embodiment this includes how a microchip can be designed and its system and methods to behave as a universal people sensor microchip for the purposes of being something that other manufacturers can embed into their products as a plug-n-play system.

In another embodiment systems and methods are provided for wirelessly transmitting a first part's personal preference. As a non-limiting example this can include a way for any first person to beam out their references to devices around them. As a non-limiting example this includes how a first person can enter how they like their coffee in an app where a first-person account holds their personal preferences, and the app will make that information available to any coffee machine or coffee shop the first person walks into. In this embodiment collecting, organizing and beaming out a first person's personal preference are provided in a universal way, not as a locked in siloed way which is how all apps/iota devices currently do things.

In another embodiment systems and methods are provided for physical access identification using facial recognition. As a non-limiting example, a way is provided to identify a first party and grant them access based on them emitting a universal ID signal that verifies who they are to the reader as a first factor. A reader with a camera uses a camera image to match the face that the first party has in its account as a second factor. Learning algorithms can be utilized to better match the face every time the first party walks into a door.

In another embodiment systems and methods are provided for physical access identification of a first party using voice recognition. As a non-limiting example, a first party Is identified and then granted access based on emitting a universal ID signal that verifies who the first party is to a reader as a first factor. The reader has a microphone and requires the first party user to say "open" to match the voice pattern to that of a pre-recorded voice pattern as part of the first party signup process. The reader then matches the voice pattern that the first party has in its account as a second factor. Learning algorithms can be used to better match the voice every time the first party walks into a door.

In another embodiment systems and methods detect tailgating activities using wireless sensors and personal devices. As a non-limiting example, a method is provided to detect if a possible tailgating event has occurred by requiring all occupants to carry with them a mobile device that emits a unique universal ID signal that represents them to a reader, paired with other sensors such as thermal imaging or people counter sensors, such that the combined data allows us to count there are two proxy users. When there are three people passing through the door one is a tailgater. Several technologies can be utilized for counting people including but not limited to WIFI, ultrasound and the like. As a non-limiting example, he combination of such technologies working with the universal ID signal helps to surface tailgating events.

In another embodiment systems and methods are provided for autonomous vehicle identification of passengers for intended locking, unlocking and personalization. As a non-limiting example this provides a method that the autonomous cars use a universal ID signal to detect if they are the right passenger they are supposed to pick up without the first party having to do anything. Since cars are required to be locked in motion, autonomous cars need a way to only unlock for the right passenger on the sidewalk such that a random person doesn't jump in the car instead. The car can also use a universal ID signal to personalize the drive experience and to show a screen identifying to the passenger that this car is allocated to that first party. In this manner the problem of one car maker and one app problem is resolved by allowing all cars to use the same universal ID signal in such a way that the car software can pull in the relevant information needed to give the passenger both a personalized experience and secure/efficient pick up and open experience.

In another embodiment systems and methods are provided for machine to machine proximity payment transactions. As a non-limiting example this covers a way for independent machines to send payments to each other without requiring credit cards or a first party to intermediate. This allows for machine to machine transactions to occur. As a non-limiting example this can include: autonomous cars to pay for parking directly to a parking meter without first party involvement, e.g., it is achieved passively.

In one embodiment an inductive charging of a lock via cylindrical latch mechanism is provided. As a non-limiting example, a charge lock device is provided by an inductive coil within a latch mechanism and coils around a slot that the latch goes into to lock a door.

In one embodiment inductive charging of lock is provided via a lock faceplate and a lock device is charged by inductive coils positioned around door/frame faceplates.

In one embodiment inductive charging of phone devices is provided on a car body. As a non-limiting example, a first party's phone is charged by placing it on the bonnet of the car, for future cars that use the first party's phone as the key as a backup when the phone is dead is can still charge and allows entrance into the car.

In one embodiment any AI (assistant AI and voice command AI) can tap the universal ID signal representing the first party queries it for useful information to serve the first party.

In one embodiment a knock can be provided on the first party's phone to trigger a command to unlock a door in proximity.

In one embodiment first party phone sensors are used to fingerprint the first party such that access to a building is only granted if it's the owner of the phone. As a non-limiting example this can be applied specifically for access control and other use cases where the first party needs to be identified by its phone.

In one embodiment a first party driver with the universal ID signal and a car with a Universal ID sensor that verifies the first party can drive the car and enabled ignition and a combination of the first party, car and garage sensing gives access to the car and first party driver for secure vehicle access.

In one embodiment an organization with a fleet of cars can authorize a driver with insurance information switches over to the car and driver for the duration of the trip. This can be used as well for a rental car situation.

In one embodiment energy harvesting is achieved via weight and coil for Beacons in high vibration environments, including but not limited to buses, cars and the like.

In one embodiment energy harvesting is provided charging door devices using a hinge of a door to charge by the motion of the open and closing swinging door to charge via gears.

In one embodiment Idea a first person's universal ID signal (from a pedestrian's phone) in traffic for cars and public transport detects pedestrians and cyclists on the road. Transport/traffic systems can use it to optimize public transport and road traffic.

In one embodiment a system presence hub is plugged into a power socket in a garage that then emits a RF signal to open the garage door as the first party drives to the garage. This requires no installation and is like how a first party programs its garage relative to obtaining a new transponder.

In one embodiment an edge system is provided that includes systems and methods to enable controller-less access control for easy installation and integration into any electrified door system.

In one embodiment background a firmware OTA update system and method are provided.

In one embodiment systems and methods allow second parties to leverage a system presence system to be able to detect their beacons without needing first parties to download their own apps.

In one embodiment a bio-chip is provided that emits the universal ID signal which allows any system to detect it and use it to serve the first party in a secure and private way.

In one embodiment a universal way is provided that provides for a car to be able to give a first party a personalized experience by detecting the universal ID signal.

In one embodiment the universal ID signal allows an augmented reality system to use it to identify and provide relevant information of people augmented in the system.

In one embodiment a cached token system and methodology are provided via the universal ID signal.

In one embodiment rotating mac addresses of mobile devices to ensure a persistent signal is achieved using the universal ID signal. Such systems can use the universal ID signal without having to track and monitor the mac address, e.g., a challenge-response exchange.

In one embodiment the universal ID signal is used for logical access as a second factor auth.

In one embodiment a FPGA is used to enable the universal sensor to be universally compatible with any embedded system by programmatically enabling it to be configured to work with any interface protocol.

In one embodiment a process is provided of using a phone's magnetometer to determine directionality at an access point, i.e. entering or exiting the door.

In one embodiment each device is represented individually by a card but accessed collectively via an app container view. Each can be selected individually and be expanded to view details and send/receive commands from the associated device.

In one embodiment two BLE radios function in a way to solve for limitations of BLE not being able to connect and interact with hundreds of other devices/phones, as is illustrated in FIG. 12. As a non-limiting example one radio tracks broadcasts presence of the reader device and scans for presence of smart devices, and the other radio is used to pair the reader devices to the smart devices, individually.

Figure 13:
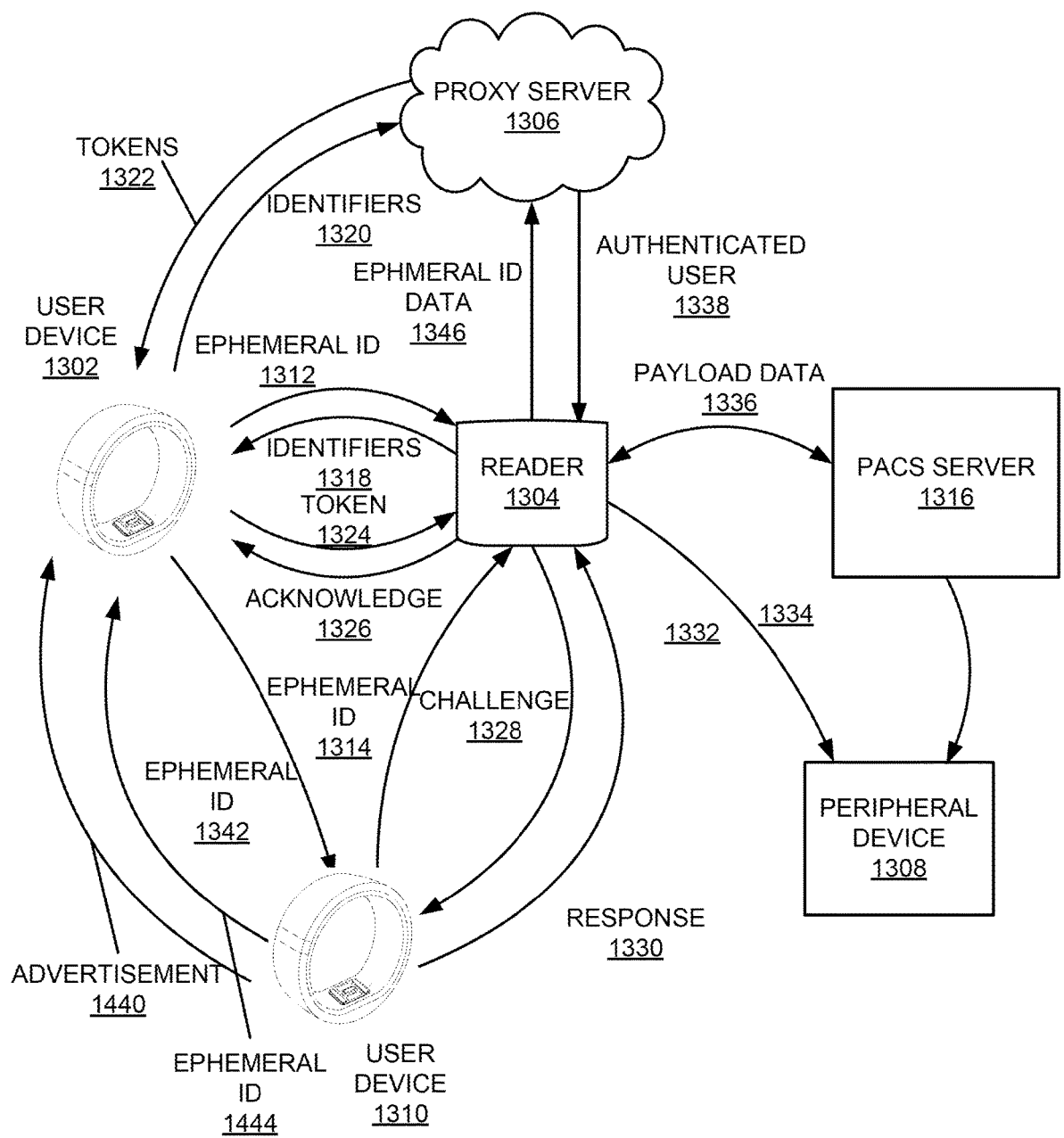
FIG. 13 is another block diagram of a reader according to various embodiments of the present invention.

In FIG. 13 systems are illustrated including a first user device (e.g. a smart phone, smart watch, ring, tablet, wearable device, augmented reality glasses) 1302 coupled to an identity reader 1304 and a cloud-based server 1306. Identity reader 1304 may also be coupled to cloud-based service 1306 and a peripheral device 1308. FIG. 13 also includes a second user device (e.g. a smart phone, smart watch, ring, tablet, wearable device, augmented reality glasses) 1310 that may be coupled to first user device 1302 and identity reader 1304. In some embodiments, identity reader 1304 may be used to control peripheral device 1308 and/or may simply be used to detect presence of user devices.

In some embodiments, a peripheral access control system (PACS) 1316 may be provided, as illustrated to control peripheral device 1308. In some embodiments, identity reader 1304 may perform several functions including scanning for nearby user devices (detecting ephemeral IDs); connecting to user smart devices; and broadcasting advertisement signals.

In some examples, the radio in identity reader 1304 is in a scanning/broadcast mode, whereby it alternates between broadcasting its presence within a geographic range, and then scanning for ephemeral ID signals (e.g. a Bluetooth device address, UWB signals) from devices that are within the geographic range of the identity reader. Next, a first user smart device 1302 detects the advertisement signals from identity reader 1304 and outputs ephemeral ID signals 1312 that are detected by identity reader 1304. In this example, if identity reader 1304 has not seen smart device 1302 before and smart device 1302 desires to control peripheral device 1308, identity reader 1304 enters a Bluetooth pairing or connection mode. In this pairing mode, a number of steps may be performed, such as identity reader 1304 receiving Bluetooth credentials, or the like. In some cases, identity reader 1304 merely wants to detect and record presence of smart device 1302 and no pairing is typically performed.

In some examples, a second user of smart device 1310 may have previously been seen by or paired with identity reader 1304, for example a hour ago. As will be discussed further below, the next time second user smart device 1310 attempts to communicate with identity reader 1304, (e.g. provide a token, provide a user selection, instruct identity reader 1304 to unlatch a door plate, provide credentials to identity reader 1304, provide input data, or the like), a more streamlined connection process (e.g. challenge 1328 and response 1330) may occur.

In various embodiments, a problem that arises when identity reader 1304 is in the process of Bluetooth pairing with first smart device 1302, the Bluetooth radio is unavailable. Accordingly, communications from second user smart device 1310 are not received or acknowledged by reader 1304 until after a delay. This delay be up to 5 or more seconds, depending upon the specific embodiments. In the meantime, the user of second user smart device 1310 may think that their smart device 1310, the identity reader 1304, security server 1306, are malfunctioning, are of low quality, are unreliable, or the like because of the delay. Further, if there are multiple user devices attempting to contact reader 1304 at about the same time, the delay may be much worse, as each user device may separately pair with to identity reader 1304.

In some embodiments, to reduce the communication delay between reader 1304 and second smart device 1310, embodiments of the present invention incorporate multiple parallel communications channels within reader 1304. In one specific example, two BLE radios and processors may be used, as illustrated in FIG. 12, although other combinations of channels are also contemplated in other embodiments, e.g. BLE and WIFI, BLE and ZigBee, BLE and UWB, UWB and WIFI, and the like.

Figure 14A:
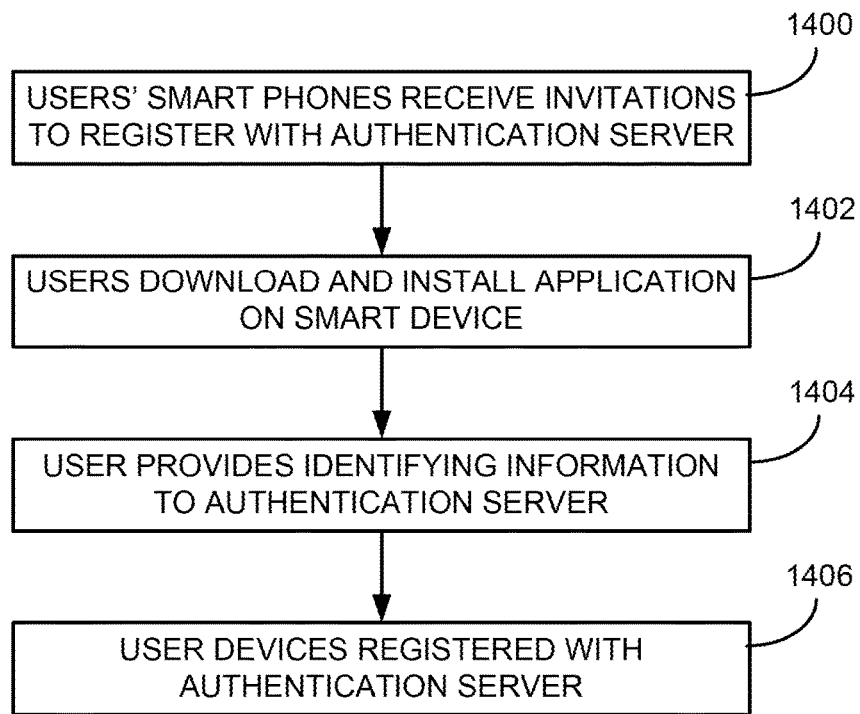
FIGS. 14A-E are flow diagrams of various process accordance with some embodiments.
Figure 14B:
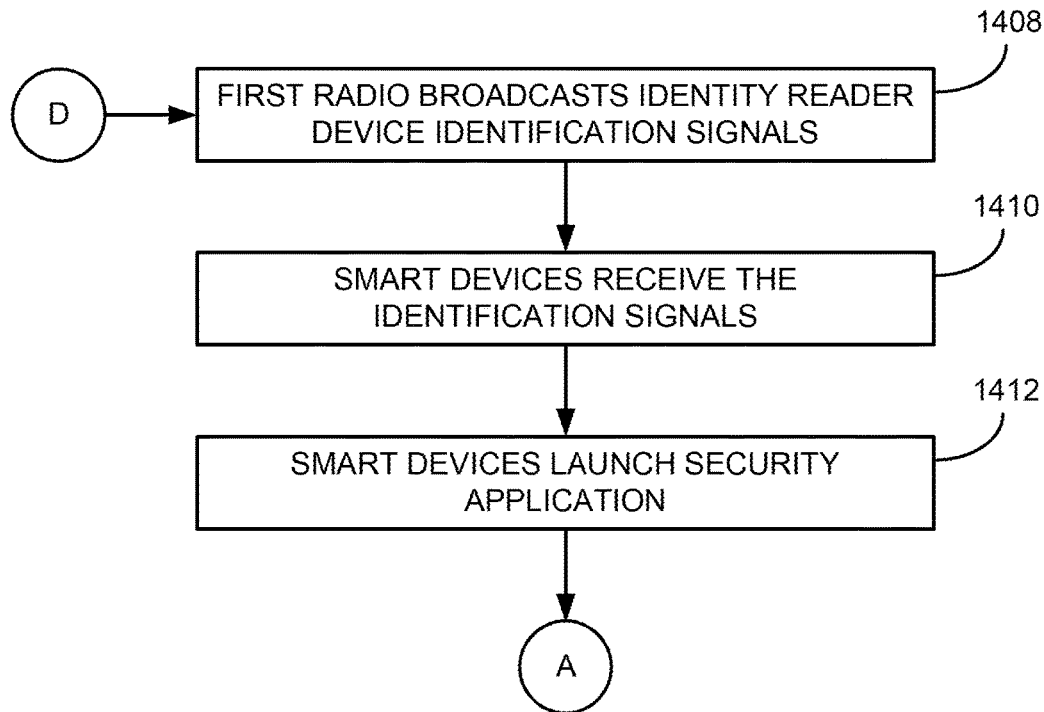
Figure 14C:
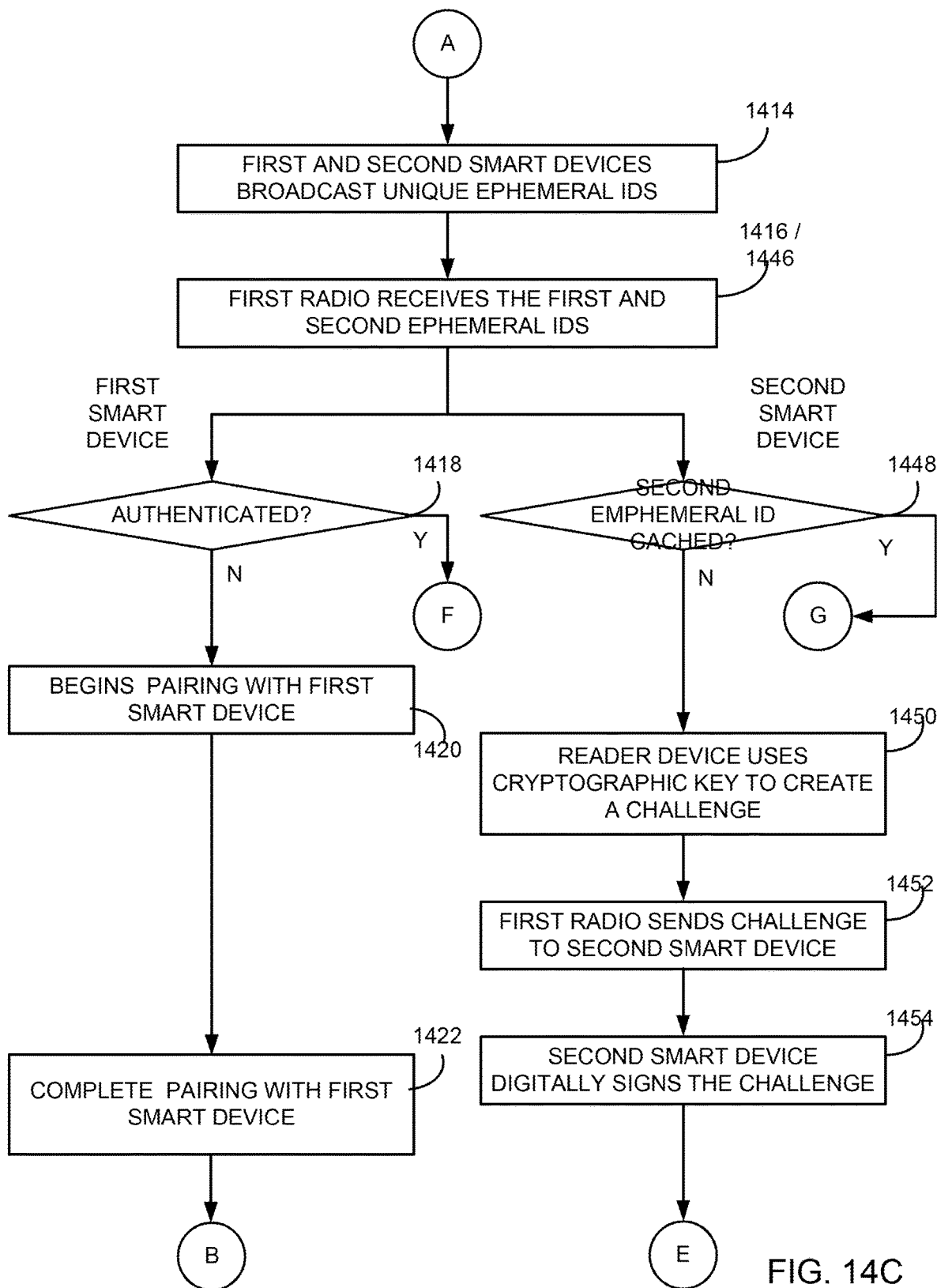

FIGS. 14A-C illustrates a block diagram of a process according to some embodiments of the present invention. To better visualize the interaction between components of embodiments of the present invention, these process steps refer to elements illustrated in FIG. 13.

In FIG. 14A, in some embodiments, upon invitation to users, step 1400, users download and install a security application on their smart-device 1302, step 1402 from an application store such as the AppStore, Google Play, and the like. In some embodiments, the security application may be an application developed by the assignee of the present patent application. Next, using the security application running upon the smart device, the users provide identifying information to an authentication server via a wide-area network to register with the cloud-based authentication service or server 1306, step 1404. As a result of these steps, the users and the users' smart devices are personally identified to authentication server 1306, step 1406. In some embodiments, biometric data may also be securely captured from the users and hashed or digitally signed by authentication server.

In some cases, a smart device such as a ring, earbuds, eyeglasses or the like may be pre-loaded with security application software, or the like. Further, some of these devices have relatively small battery life so communication between these wearable devices and the authentication server may be facilitated by another smart device, such as a smart phone or the like.

In FIG. 14B, initially identity reader 1304 broadcast advertisement signals using one of its short-range radios (e.g. a first radio—BLE), step 1408. In some embodiments, advertisement signals may identify the identity reader as being associated with the authentication service and may uniquely identify itself. Next, in some embodiments, user devices (smart devices) may receive the broadcast signals from identity reader 1304, step 1410. In some cases, security application discussed in step 1402 may be launched, if the security application is not already running on the smart devices, step 1412. In some embodiments, the security application may be an application developed by the assignee of the present patent application. In some examples, the security application installs a hook in the operating system, such that certain actions may occur when the operating system detects advertisement signals from identity readers. In one case, the security application or portions of the application may automatically be launched by the operating system. In other examples, the user may manually run the security application, or the like.

In some embodiments, time-stamped advertisement signals received by smart devices may be stored within the user smart device. For example, as a user goes through out their day, their smart device may sense and store a series of identifiers for reader devices that are sensed. As will be described below in FIGS. 16A-B, such data may be used for a variety of purposes.

In some embodiments, when the security application runs upon the first smart-device and second smart device, the smart-devices broadcast 1312 and 1314 responsive ephemeral IDs, typically via a short-range transceiver, e.g. Bluetooth Low Energy (BLE), UWB, or the like, step 1414. As described above, the ephemeral IDs are not permanently associated with the users. In some embodiments, the ephemeral IDs may include unique MAC addresses, that may be changed by the smart devices over time. In some embodiments, smart rings or other lower power devices may directly output the ephemeral IDs to the identity readers, and in other embodiments, smart devices paired to these lower power devices may broadcast their ephemeral IDs in response.

Figure 14D:
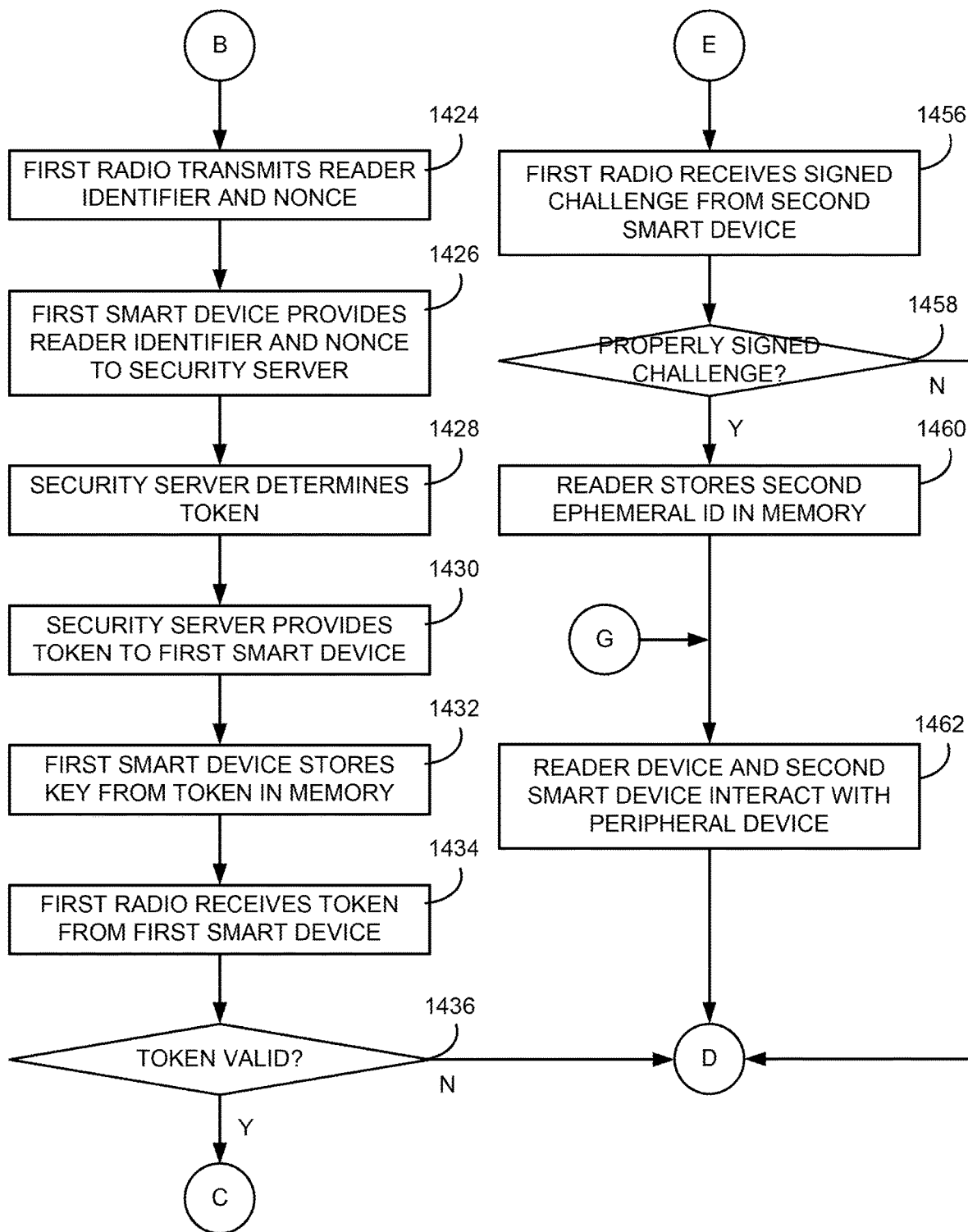

In some embodiments, there may be one or more communications channels available on the identity reader 1304. In FIGS. 14C-D, the processes for the first smart device 1302 and the second smart device 1310 may thus occur asynchronously or at the same time, if pairing is desired.

In various embodiments, when the first smart device 1302 is within the broadcast range of the identity reader 1304, the identity reader 1304 may use a first radio to capture or sense the first ephemeral ID 1312 from the first smart device 1302, step 1416. Next, identity reader 1304 may determine whether the first smart device 1302 is currently authenticated with identity reader 1304, step 1418. In some embodiments, step 1418 may include determining whether the smart device has any tokens cached, whether the first ephemeral ID 1312 is already cached within the identity reader 1304, or the like. Further details for such operations will be discussed below with respect to a second smart device 1310.

In various embodiments, if there is no active session, the identity reader 1304 may begin a pairing process with the first smart device 1302, step 1420. In one example, the second radio in the identity reader 1304 may be used for the pairing process. In some embodiments utilizing BLE, the conventional Bluetooth BLE pairing process (including exchanging keys, and the like) may take some time, e.g. typically 2 to 5 seconds. In various embodiments, if successful, the pairing process ends with step 1422.

Turning to FIG. 14D, in some embodiments, the following steps may occur after the first smart device 1302 is paired. Initially, the first radio of the identity reader 1304 may send the first smart device an identifier 1318 of the identity reader and additional data (e.g. nonce, random number, pseudo random identifier), step 1424. A nonce, or other random or pseudo random number may be used to reduce the possibility of a replay-type attack. The first smart device 1302 may then provide 1320 the identifier, the nonce, the first ephemeral ID to the cloud-based security server 1306 in step 1426. In various embodiments, this is performed automatically by the first smart device 1302 running the security application program. Further, in some embodiments, this communication may be performed via cellular radio communications, WIFI, mesh network, SMS or the like.

In various embodiments, authentication service 1306 may maintain an association between ephemeral IDs and user identifiers with respect to time. This association data may be maintained in encrypted form within authentication service 1306. As will be described below, the association data may be stored along with identity reader 1304 usage data, smart device 1302 usage data, smart device 1310 usage, and the like, and these data may be used for health tracking applications, or the like.

As was previously discussed in some embodiments, in response, the authentication service or server 1306 may take the identifier, nonce, data associated with the users of the first smart device 1302, and the like to form one or more unique tokens for the user, step 1428. In particular, authentication server 1306 may first determine whether the user is authorized to access identity reader 1304 by determining whether the user is included in one or more security policies, subscription services, or the like. If so, authentication server 1306 may digitally sign or encrypt data that includes data such as the ephemeral ID, the nonce, the identifier of the identity reader, time stamps, and the like to form one or more tokens. In some embodiments, the data is encrypted with a private key associated with authentication server 1306. In such cases, identity readers (e.g. 1304) are provisioned with a public key associated with authentication server 1306 and may use the public key to decrypt the token, as will be described below.

In various embodiments, the one or more tokens are then provided 1322 to the security application program on the first smart device 1302, typically via the same communications channels as step 1426, step 1430. In various embodiments, data stored in a payload of the token 1322 may also include one or more additional cryptographic keys. In some examples, the cryptographic key may be a symmetric key, a cryptographic key pair, or the like. At least one of the additional cryptographic keys may be stored and maintained upon the first smart device 1302, step 1432.

In cases where the user has a smart ring or other lower power device, steps 1420-1432 may be performed by the smart ring or the like, itself, or may be performed by a smart device, e.g. smart phone that has been paired to the lower power device. In such embodiments, once the token is received by the paired smart phone, it may be uploaded to the smart ring, or the like.

In some embodiments, the token is then passed 1324 from the smart ring, smart phone, or the like to the identity reader 1304 via the first radio, step 1434. In response to the token, the identity reader 1304 determines whether the token 1322 is valid/the user is authenticated, step 1436. In some embodiments, all or a portion of the token is encrypted (or digitally signed) by the security server 1306 possibly using the reader identifier, nonce, and the like. In this step, the identity reader 1304 may attempt to decrypt portions of the token or attempt to verify the digital signature in order to determine whether the token is valid/determine if the user is authenticated.

Figure 14E:
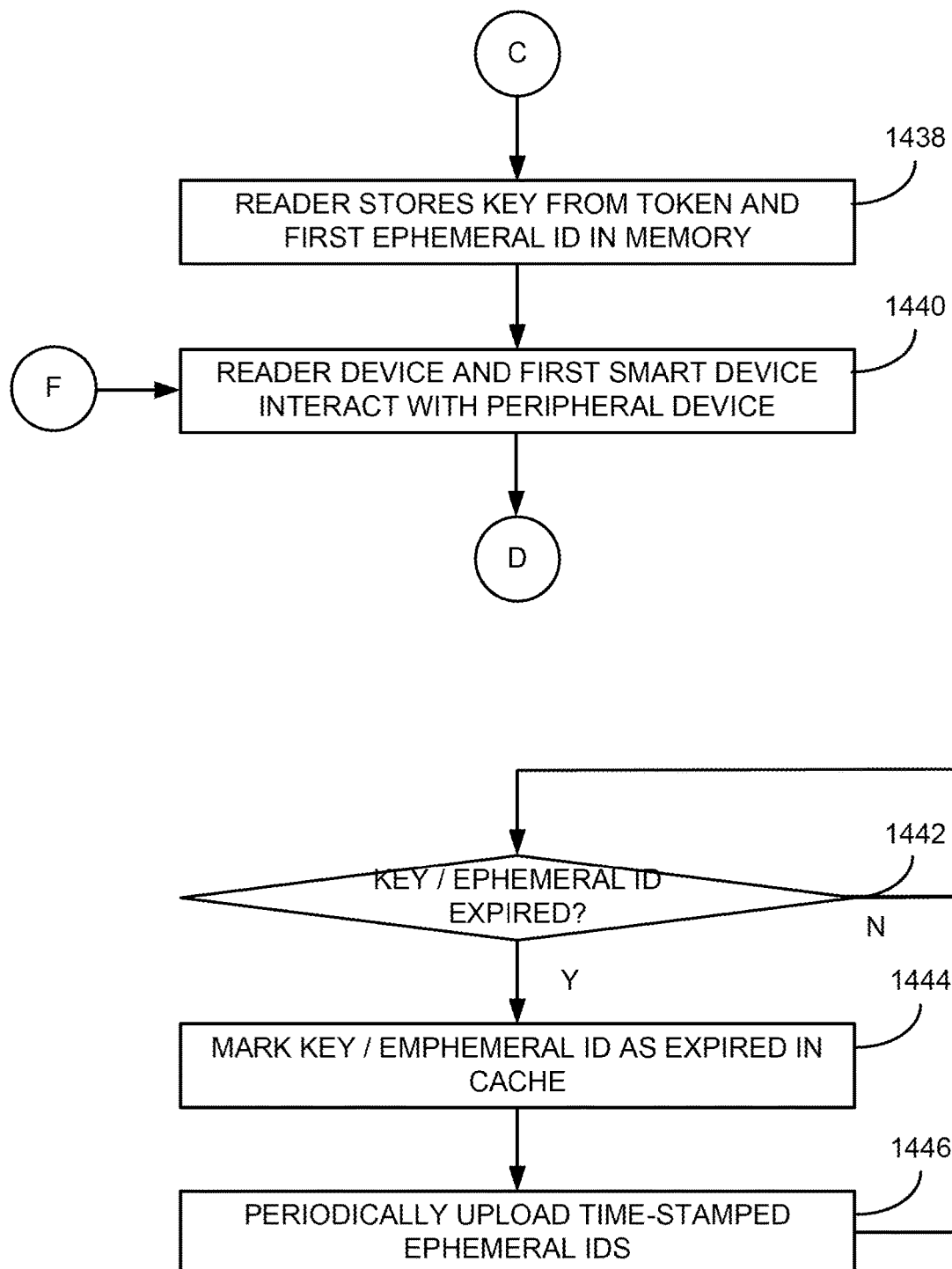

Next, as illustrated in FIG. 14E, in various embodiments, the one or more additional cryptographic keys stored in the payload portion of a token, as well as the first ephemeral ID associated with the first smart device 1302 may be stored or cached in the memory of identity reader 1304, step 1438.

After validation of the token, identity reader 1304 may direct 1332 a peripheral device 1308 to perform a user perceptible action, step 1440. For example, the identity reader 1304 may unlatch a door, display a custom greeting to the user, enable a keyboard, authorize a financial transaction, and the like. In other embodiments, identity reader 1304 may present the first smart device 1302 with one or more user-selectable actions that can be performed by peripheral device 1308, and the user may select one or more actions from within the security application, by performing gestures, or the like. In still other embodiments, peripheral control server 1316 may be used to control peripheral device 1308, e.g. a legacy control access system. Accordingly, identity reader 1304 may provide instructions 1336 directly to PACS 1316.

In some embodiments, after completion of the user-perceptible activity, identity reader 1304 may also provide 1326 an acknowledgement signal back to user device 1302. In some cases, the user of smart device 1302 may receive feedback in response to the acknowledgement signal, in the form of an illuminated LED (e.g. red or green depending upon success), a vibration signal, an audio output signal, and the like.

In various embodiments illustrated in FIG. 15E, a separate process in the identity reader 1304 may be performed. In particular, time stamped data stored in step 1438 (e.g. one or more cryptographic keys, ephemeral IDs, etc.) may be stored or cached for a limited amount of time, for example 1 hour, 2 hours, 8 hours, 24 hours, or the like. In one process, when these time stamps are expired or in the past, step 1442, they may be flushed from the cache or marked as invalid, step 1444. In other embodiments, these data may be deleted or written over only if new data (e.g. ephemeral IDs, and like) needs to be cached, or the like.

In some embodiments, ephemeral IDs seen by identity readers 1304 may be uploaded to authentication server 1306 as usage data, step 1446. As merely an example, fifty users of different smart devices using embodiments of the present invention walk down a hall and pass identity reader 1304 during the day, but only ten of these users interact with peripheral 1308 (e.g. opening a controlled access door). In various embodiments, the ephemeral IDs for all fifty smart devices along with associated time stamps will be stored in identity reader 1304. In other embodiments, the ephemeral IDs and time stamps for only the ten users above, may be stored. In either case, these data may or may not be encrypted within identity reader 1304, for example using a public key associated with authentication server 1306. Periodically, these usage data may be uploaded to authentication server 1306. In some cases, identity readers 1304 may use WIFI, a mesh network, or the like to upload the usage data to service 1306. In other embodiments, the usage data may be provided to a local smart device or to a user smart device, and these devices in turn may facilitate the upload of the usage data to the authentication service 1306. As will be discussed below, in some embodiments, this usage data may be for health tracking purposes, or the like.

Returning to FIG. 14C, in various embodiments, when the second smart device 1310 is within the broadcast range of the identity reader 1304, the identity reader 1304 may also use the first radio to detect the second ephemeral ID 1314 from the second smart device 1310, step 1446. In various embodiment, as steps 1416 and 1446 take a short amount of time, any delay introduced by the first radio performing one step before the other step is not typically appreciable. In some cases, a low-power device, such as a smart-ring may perform this step directly or may be performed by a paired smart phone, or the like.

In some cases, while the second radio of identity reader 1304 is pairing with the first smart device 1302, as is illustrated beginning in step 1420 and ending in step 1422, the first radio of the identity reader 1304 continues to operate and may interact with the second smart device 1310.

Next, in some embodiments, identity reader 1304 may determine whether the second smart device 1310 is currently authenticated with identity reader. In some embodiments, determining authentication may begin with determining whether the second ephemeral ID 1314 is already cached within the identity reader 1304, or the like step 1448. As was discussed in step 1438, once smart devices provide a valid token to the identity reader 1304, token keys, ephemeral IDs, and the like may be cached within the identity reader 1304.

Further, as discussed in steps 1442 and 1444, this data is may be cached for a limited amount of time. Accordingly, in step 1448, if the second ephemeral ID 1314 is present in the cache of identity reader 1304, the second smart device 1310 may be authenticated.

In some embodiments, in addition to determining that second ephemeral ID 1314 is present, identity reader 1304 may also require a second factor authentication. In some embodiments, this may include the user using their biometrics (e.g. fingerprint, facial data, blood vessel data, etc.), a PIN, or the like to unlock their device or the security application. In other embodiments, data may include other collected biometric data (e.g. gait, performance data (e.g. gestures), etc.), GPS tracking data, lists of recently encountered identity reader devices (e.g. identifying routine/habitual behavior, etc.), or the like. In various embodiments, these types of second factor authentications may be used by identity reader 1304 to help verify that the second ephemeral ID 1314 is truly provide by smart device 1310.

In various embodiments, the second ephemeral ID may not be cached in the identity reader 1304 memory, although the second smart device 1310 had recently paired with the identity reader 1304. In some examples, this may be due to the ephemeral ID 1314 of the second smart device rotating or changing to another ephemeral ID. This often occurs for the sake of privacy. As an example of this, at 9 O'clock, a smart device may have presented a first ephemeral ID and a valid token to the identity reader that is good for a 6-hour session, and the first ephemeral ID and portions of the token are cached. Then at 10 O'clock, the ephemeral ID of the smart device changes into a second ephemeral ID. If the smart device then approaches the identity reader at 11 O'clock, the identity reader does not recognize the second ephemeral ID, as only the first ephemeral ID was cached.

In such cases, the following steps may then be used to determine whether the second smart device 1310 is authenticated. More specifically, the identity reader 1304 may first create a challenge, step 1450. The challenge is then sent 1328 to the second smart device 1310, using the first radio, step 1452. In various embodiments, the challenge may be a random character string, a predetermined character string, an encrypted string, a nonce or the like. In response to the challenge 1328, the second smart device 1310 may use the cryptographic key stored in the payload of the previous token (e.g. step 1432) to encrypt the challenge, digitally sign the challenge, or the like, step 1454. In some embodiments, with a low-power device such as a smart ring, or the like, these steps may be performed upon a smart phone, or the like that is paired to the smart ring, or the wearable device itself. The signed challenge response 1330 is typically received by the identity reader 1304 via the first radio, step 1456.

In some embodiments, the identity reader 1304 may use the cryptographic key previously cached to determine whether the response 1330 is valid, step 1458. In some embodiments, the cryptographic keys may be symmetric, a key pair, or the like. In other embodiments, a hashing algorithm with a nonce, or the like may be used for verification purposes. In some examples, if the challenge 1330 was properly signed, the identity reader 1304 may update the cache with the second ephemeral ID 1314, step 1460. As can be seen from the above, caching of ephemeral IDs and comparing ephemeral IDs is a computationally more efficient way to determine whether a session exists for an incoming smart device. If the ephemeral IDs are cached (possibly along with the second factor authentication discussed above), this challenge and response steps may not be needed.

In other embodiments, instead of the challenge and response, the second ephemeral ID may alternatively be sent 1346 to authentication server 1306. If the ephemeral ID is not cached, but is associated with an authenticated user within authentication server 1306, an identifier associated with the user as well as an authorized signal 1338 may be returned to reader 1304.

In the present embodiments, once the session with the second smart device 1310 is validated, the identity reader 1304 may direct a peripheral device 1308 to perform a user-perceptible action 1334, step 1462. For example, it may allow a user of the second device 1310 to open a security door, it may display relevant information to the user on a display (e.g. name, a welcome screen, an itinerary, etc.), it may activate a key pad; it may allow a user to select from one or more options for the peripheral (e.g. open a door, lock a door, start a vehicle, turn on air conditioning, etc.); and the like.

In some embodiments, identity reader 1304 may record the ephemeral IDs from smart devices 1302, 1310 or the like, as those respective users are simply walking by identity reader 1304. This data, ephemeral IDs along with time stamps may be optionally encrypted and then uploaded to authentication service 1306 for a number of reasons. In some cases, this data may be used for health tracking purposes; to determine usage patterns for users (e.g. for building a behavioral model); and the like.

In various embodiments, as illustrated in FIG. 13, payload data 1336 may be provided to a back-end server associated with identity reader 1304. The payload data 1336 may include a persistent ID that identifies the user to the system coupled to the identity reader. The persistent ID may include a customer frequent flyer number, a customer loyalty card number, a debit or credit card, a stored value card, an employee ID number, and the like. In some examples of interaction, the user may purchase something using the stored value, debit or credit card; the customer can check-in to a location; the user can log into a computer or other electronic device; the user can log into an account (e.g. Netflix, Amazon); the user can enter a controlled access area; the user can pass through security, and the like. Additional examples of interactions between the identity reader and the smart device, as well as preferences and other data stored in the payload data, or the like, are described herein.

Figure 15:
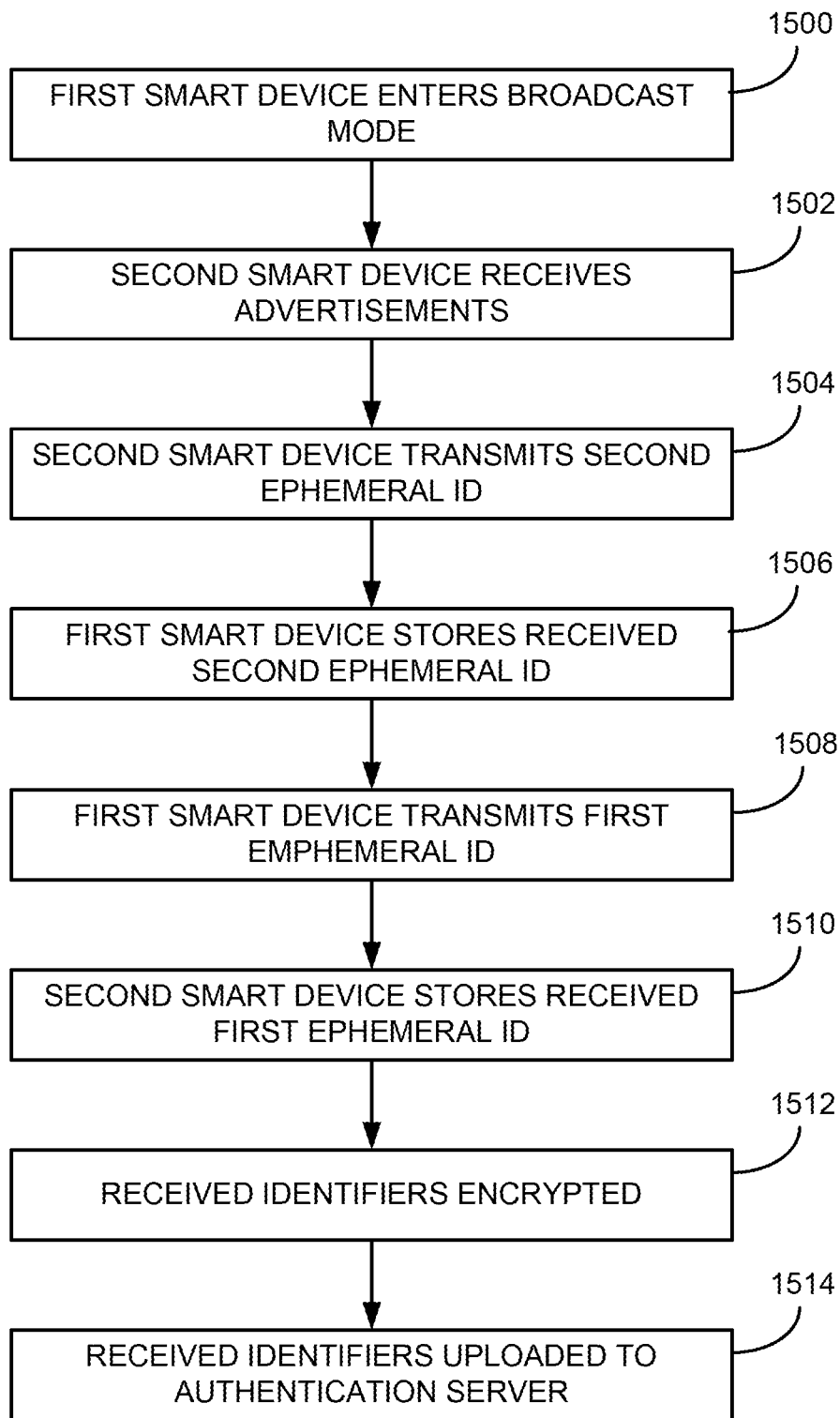
FIG. 15 is another block diagram of a process according to various embodiments of the present invention.

FIG. 15 illustrates a block diagram of a process according to various embodiments. More specifically, FIG. 15 illustrates user device to user device interaction, referring to elements in FIG. 13. Initially, the process occurs after FIG. 14A, where the smart devices have registered with authentication server 1306.

Next, in various embodiments, another smart device (e.g. a smart device (e.g. 1310), identity reader device (e.g. 1304), a kiosk, a check-in smart tablet, etc.) may enter an advertisement mode, step 1500. This may be similar to step 1408 in FIG. 14B. Next, another smart device (e.g. 1302) receives the advertisement signals, step 1502. In various embodiments, in response to the advertisement signals, the other smart device 1302 outputs 1342 its ephemeral ID, step 1504. This ephemeral ID may then be stored on the broadcasting device (e.g. user device 1310 or identity reader 1304), step 1506.

In various embodiments, in response, the broadcasting device transmits its identifier, step 1508. In embodiments where the broadcasting device is smart device 1310, the first ephemeral ID is output 1444, and where broadcasting device is identity reader 1304, the identity reader identifier is output

1318. The broadcaster's identifier is received by user device 1302 and may be stored, step 1510. For example, the ephemeral ID of user device 1310 and time stamp may be stored within user device 1302; the ephemeral ID of user device 1302 and time stamp may be stored within user device 1310; the identifier of identity reader 1304 may be stored within user devices 1302 and 1310; and the like. In some embodiments, to increase privacy, the ephemeral IDs or the identity reader identifiers that are sensed may be encrypted, step 1512. In some examples, a public key associated with authentication service 1306 may be used to encrypt the data, a private key associated with the smart device, or the like.

In various embodiments, next, periodically, the devices (e.g. user device 1302, user device 1310 and identity reader 1304) may upload the list (a contact log) of time stamped ephemeral IDs and identifiers for identity readers (e.g. usage data or sensed data) to authentication service 1306, step 1514. In some embodiments this data may be uploaded whenever the user device contacts authentication service 1306 for any other reason. For example, when user device 1302 requests a token from authentication service 1306, the list of ephemeral IDs sensed may also be uploaded; when identity reader 1304 passes 1346 ephemeral ID data to authentication server 1306 for a look-up operation; or the like. In other embodiments, the upload may be periodic, e.g. every day, every week, etc., upon demand, when system resources are low, upon request of the user of the smart-device, or the like.

Figure 16A:
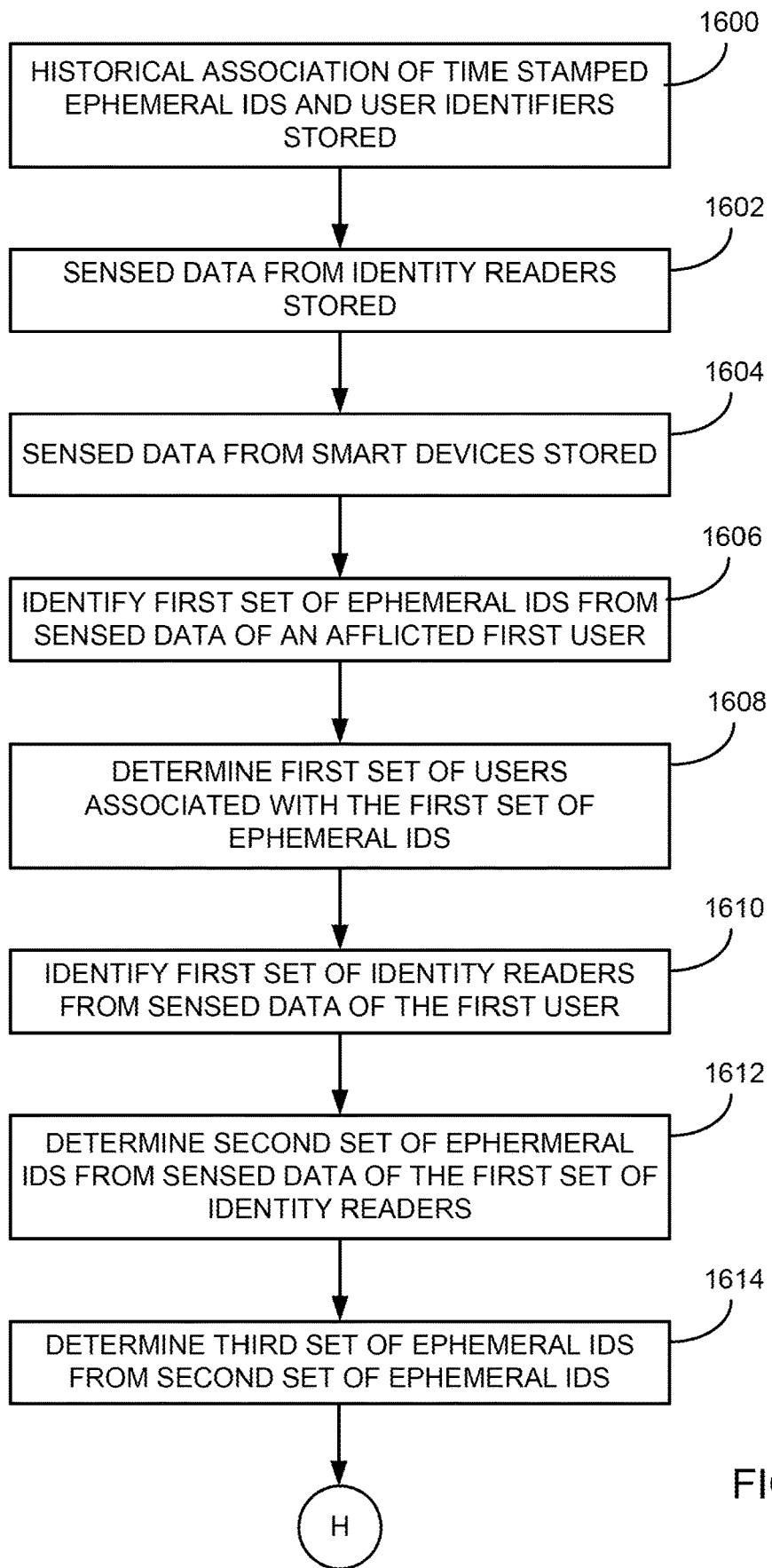
FIGS. 16A-B are flow diagrams of various process accordance with some embodiments.
Figure 16B:
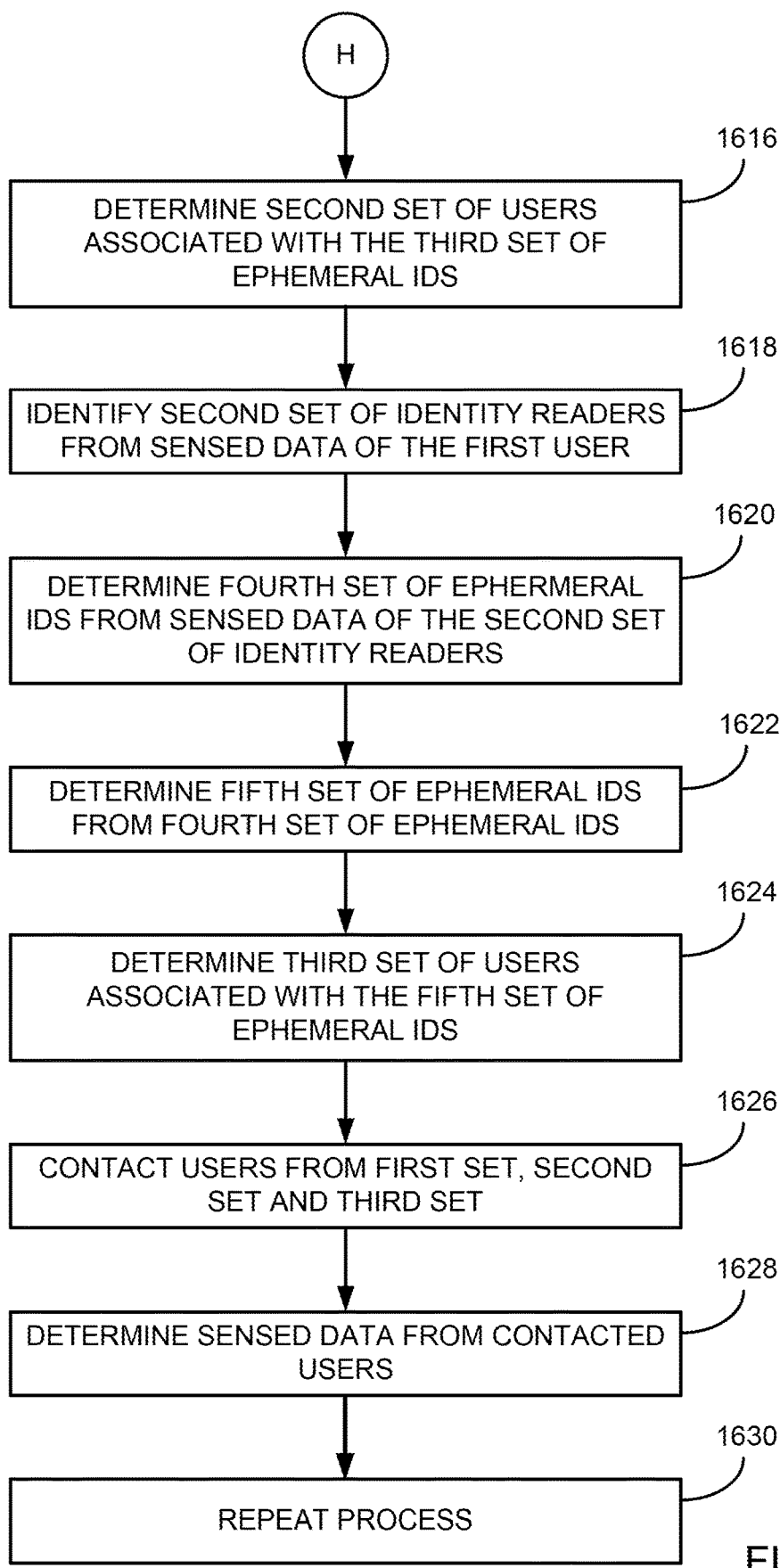

FIGS. 16A-B illustrate a block diagram of a process according to various embodiments. More specifically, FIGS. 16A-B illustrate a method of tracking user interactions. Initially, authentication service 1306 stores historical association data between time stamped ephemeral IDs, actual user identifiers (e.g. email address, telephone number, username, or the like), step 1600. This data is obtained, when users register their smart devices with authentication service 1306, and when these smart devices periodically provide 1320 data to authentication service 1306 as part of a request for services. This association log data may be encrypted with a public key of authentication server 1306, or the like.

It is believed that such embodiments are more secure than simply providing a unique identifier for each smart device, that does not change. For example, if a fixed unique identifier for a specific smart device is provided, anywhere in a database where the fixed unique identifier is found, the data stored therein can be traced to the specific smart device. In contrast, in various embodiments, as a smart device may output any ephemeral IDs, an occurrence of any particular ephemeral ID in a database cannot be traced to a particular user. As described herein for some examples, only if a particular time stamp/ephemeral ID pair is specified, can a specific smart device be determined. Accordingly, embodiments of the present invention provide a high level of security.

Additionally, authentication service 1306 stores the sensed data or usage data from identity reader devices, such as identity reader 1304, step 1602. As describe above, this usage data typically includes a list of time stamped ephemeral IDs of user devices seen by the smart devices. Because the geographic locations of these identity readers are known, i.e. are stationary (a check-in kiosk, a controlled access door or gate, etc.), the novel concept of determining geographic near misses is now enabled. Additionally, authentication service 1306 stores usage data or sensed data logs from smart devices, such as user devices 1302, 1310, etc., step 1604. As described above, these usage data also typically includes a list of time stamped ephemeral IDs sensed by the respective smart devices, and may include a list of time stamped identifiers (e.g. advertisement data, etc.) associated with identity readers also sensed by the respective smart devices.

The above data may be stored in an encrypted form, for example, with a public key of authentication service 1306, a private key of a smart device, or the like. It is contemplated that this data may decrypted upon authorization or pre-authorization of the users, for example as part of a terms of service agreement. In addition to or alternatively, this data may be decrypted upon declaration of an emergency, i.e. health emergency, national security emergency, a properly issued governmental warrant, or the like. In operation, authentication services 1306 may process the stored data to respond to authorized queries.

Various embodiments are described below with reference to an example situation: if a first user becomes sick with a contagious disease or chemical agent while working at a company. In this example, a first step for an authentication service, or the like may be to retrieve the list of time stamped ephemeral IDs (a first set of ephemeral IDs) sensed by the first user's smart device from memory or from the user's smart device. Next, based upon the historical association data or log of the first set of ephemeral IDs, actual user identifiers, and the like stored in authentication service 1306, the actual users associated with the first set of sensed ephemeral IDs at the specified times are identified, step 1608. In other words, this process determines users with whom the first user comes in very close contact with.

Next, in various embodiments, a list of time stamped identifiers (e.g. advertisement signals, etc.) of a first set of identity reader devices sensed by the first user's smart device is retrieved, step 1610. In the example above, the first user not only goes to work at his company's location, but may also visit other businesses during the day that have identity readers (e.g. a particular Starbucks, Safeway, Hilton Hotel, etc.). In various embodiments, the usage data sensed by each of the first set of identified readers (e.g. a second set of ephemeral IDs) may be determined from the user's contact data or log, step 1612.

In various embodiments, because the number of ephemeral IDs in the second set of ephemeral IDs may be large, the number of ephemeral IDs to process is reduced to a third set of ephemeral IDs, step 1614. The reduction is advantageous to authentication server 1306 as it increases the processing speed, reduces the number of computations required, and reduces the memory load. In some embodiments, a range of times about the same time the first user was sensed by the first set of identity readers is used to reduce the second set of ephemeral IDs.

In some examples, a time period may be selected to begin before the time stamp of when a first identity reader was sensed, for example from 5 to 10 minutes, or the like and may be selected to end a period of time afterwards, for example from 5 to 30 minutes, 1 hour to 2 hours, or the like. These time periods may be modified based upon type of issue based. For example, with a highly communicable disease or chemical agent, the time periods may be longer; with non-health issues, the time periods may be shorter; or the like. In the example above, if the first user enters a controlled-access elevator at Noon, the time period of interest may be noon to 12:20; if the first user buys coffee at a POS system at 3, the time period of interest may be from 2:45 to 3:15; if the person disembarks an airplane at 7 after a 5 hour flight, the time period of interest may be from 2 to 9; and the like.

After the time search windows have been reduced, the third set of ephemeral IDs may be determines referring to the associated time stamps of the second set of ephemeral IDs. Next, based upon the historical association data log that includes time stamped ephemeral IDs and user identifiers, including the third set of ephemeral IDs and associated user identifiers, and the like, the actual users associated with the third set of sensed ephemeral IDs are identified, step 1616. In other words, this process determines users who may be a geographical near miss with respect to the first user.

In some embodiments, the usage data from a second set of identity reader devices within the organization or company associated the first user may also be retrieved, step 1618. These steps may be used in addition to the above analysis of first set identity readers as desired. Similar to the above, it is expected that each identity reader device within a company has uploaded a list of time-stamped ephemeral IDs it senses (e.g. every day, every week, or the like) to form a fourth set of ephemeral IDs, step 1620. Similar to the above, the fourth set may be reduced to a fifth set of ephemeral IDs by specifying time periods around the same time the first user was sensed, or the like, step 1622. For example, if the first user's ephemeral ID is not detected at any controlled access point, no identity reader devices may initially be queried; if the first user's ephemeral ID is detected only in one building or in one location in a building, identity reader devices for other buildings or other locations in a building, may initially be ignored; and the like. Next, based upon the historical association data of the fifth set of ephemeral IDs, actual user identifiers, and the like stored in authentication service 1306, the actual users associated with the fifth set of sensed ephemeral IDs are identified, step 1624. In other words, this process also determines users who may be a geographical near miss with respect to the first user.

In various embodiments, the users who are identified above (e.g. from the first set of ephemeral IDs, the third set of ephemeral IDs, and the fifth set of ephemeral IDs) (e.g. a second user) may then be contacted by health department officials, or the like to discuss their contact with the first user and possible infection with the communicable disease, step 1626. Privacy of the first user may be maintained, as the contact may simply indicate the time of contact, in some cases the place of contact and type of possible health issue.

In turn, the list of ephemeral IDs and/or identity reader identifiers sensed by the second user's smart device may be retrieved, step 1628, and the process repeated for users in contact with or geographical near miss with respect to the second user, for example a third and fourth user, and so on, step 1630. In various embodiments, the process may be repeated to any desired contact depth, e.g. three, four, five, or the like.

In some embodiments of the present invention the above concepts may also be integrated with contact tracing functionality provided by third-party providers, such as Apple and Google. In particular, the geographic near miss capability can be used to enhance such third-party tracing functionality without relying on power intensive GPS functionality.

In some embodiments, the process of providing tokens from an authentication server to a smart device, and presenting the token to the identity reader to facilitate a user-perceptible action may not be performed. In a more streamlined approach, as ephemeral IDs are received by an identity reader, the identity reader may directly contact an authentication server to simply record the smart devices' presence. In another embodiment, authentication server may reply with an authorized signal and data associated with the user, e.g. name, picture, guest of name, etc. and the identity reader may display such data on a peripheral device. Such systems may be embodied as a visitor system. In another embodiments, the identity reader may be integral to the peripheral device, e.g. an iPad or other smart tablet.

In various embodiments discussed above, in steps 1506 and 1510, user devices store an indication of other devices that are within their respective advertisement ranges. The extent of this range may be quite large in some embodiments utilizing BLE, UWB, ZigBee, or the like. In light of this, some embodiments may utilize different factors in determining whether to log a contact with another user or not.

In some embodiments utilizing BLE, for example, signal strength may be used as an indicator of how close two users are. Accordingly, in some examples, if the signal strength exceeds a predetermined threshold signal strength, the two users' devices may store the contact about the other in memory. Otherwise, the contact may not be logged. In some embodiments utilizing UWB or ZigBee, for example, distance computation measurements may be used for determining contact. In these examples, if the two smart devices (e.g. smart rings, smart phones, etc.) are within a certain distance of each other (e.g. 10 feet, 2 meters, etc.), the two users' devices may store the contact about each other in memory. Otherwise, the contact may not be logged.

In additional embodiments, other factors may be combined with the closeness measurements, described above. In one embodiment, the duration of contact may be also be considered to determine whether to log a contact or not. As one an example of this, in addition to two users being within a threshold distance or signal strength of each other, their devices must be within that threshold for a period of time, e.g. 5 seconds, 10 seconds, or the like. Otherwise, the contact may not be logged. In another embodiment, the distances apart and the duration may be combined, integrated, or the like. Some examples of when contact logging may occur for such embodiments includes: after two users are 10 feet apart for 20 minutes; after two users are 6 feet apart for more than 30 seconds; after two users are 2 feet apart for more than 5 seconds; and the like.

In some embodiments, additional factors may include density of the users (as indicated by smart devices) proximate to each other. For example, if two smart devices are within a distance (e.g. 10 feet) of each other for an amount of time (e.g. 3 seconds), the contact may not be logged; however, if five smart devices are within the same distance (e.g. 10 feet) of each other for the same amount of time (e.g. 3 seconds), the contacts may be logged. In other embodiments, other factors that may be considered may include the ambient temperature, time of day, day of week, weather conditions, and the like.

In some embodiments, in addition to logging a contact, based upon one or multiple of the factors described above, the users may be given instant feedback via their smart device. For example, if two users are too close to each other for too long, for example while eating lunch, their smart devices may both provide an audible, visual, haptic or other proximity alert. As examples, the application running upon a smart phone may output a system notification banner; a smart ring may flash a yellow LED light; a smart watch may vibrate; a smart earbud may play a notification chime; and the like.

In some embodiments, an additional factor may include whether the contact occurs within a region, location, building or other facility subject to heightened health standards. As an example, it is envisioned by the inventors that companies, businesses, governments, health care facilities or the like may require its workers to monitor their health and report if they get sick, as such organizations desire to reduce and limit the spread of diseases within them. In light of this, in some embodiments a contact logging and contact tracing process, as described above, may be desired. As an example of this, while the worker is within the facility, the application running upon the smart device may perform some or all of the contact logging functions described herein.

In various embodiments, to promote the user contact logging within an organization's facilities, a number of check-in locations may be provided. In one example, as described above, a number of identity reader devices are installed to control peripheral devices, such as an automatic door, automatic gate, controlled access point, a computer, computer services, and the like. In such examples, in addition to the smart device providing a valid token, a cached ephemeral ID, or the like to the identity reader, described above, a status flag or bit may be sent to the identity reader. The status bit may indicate whether that the contact logging application is operating or running upon the smart device. In such cases if there is a valid token and: if status flag bit indicates that the contact logging application is not running, the reader device may not direct the peripheral device to operate; and if the status flag bit indicates that the application is running, the reader device may direct the peripheral device to operate. In some embodiments, if the peripheral device does not operate, the user may be directed to run the contact logging application, and to try again.

In still other embodiments, an additional status bit may be provided to indicate whether the user's health has been "normal" for the last two weeks, or the like. In some embodiments, a smart wearable device may collect user data (i.e. heartbeat, EKG, temperature, blood oxygen saturation, respiration rate, or the like) for determination of a baseline health model (e.g. using machine learning), and subsequently collected user data may be compared against the user baseline health model. In such examples, if the user's health is consistent with their health model for a certain amount of time (e.g. last two weeks, or the like), the smart wearable device may set the additional status bit, or have the paired smart device set the additional status bit. If the user is running a fever, or the like, the additional status bit may be cleared. In operation, this additional status bit may be used by the reader device (or kiosk device discussed below) to determine whether the peripheral device should be activated. In some examples where the additional status bit is set, the peripheral may be operated and where the additional status bit is cleared, the peripheral device may not operate.

In additional embodiments, another type of check-in location may include a kiosk (e.g. check-in tablet, or the like). These embodiments may include some identity reader-type functionality, and may or may not require tokens from the users' smart devices. In some examples, the kiosk or check-in tablet may read the ephemeral ID provided by the user's smart phone, transmit the ephemeral ID to an authentication server (possibly facilitated by another computer), receive data associated with the user from the authentication server (again, possibly facilitated), and display data back to the user, as was described above. For example, the kiosk or tablet may sense a worker's (e.g. employee, contractor, temp) smart phone and display a welcome screen for the user including, for example their name and picture. In the case where the user is a guest or a visitor, as also discussed above, the welcome screen may include a name of an internal contact, an itinerary, or other type of information. In still other embodiments, the kiosk may direct additional actions, such as the notification of another person that the visitor has arrived, reserving a conference room for the user, unlocking a controlled access point, or the like.

In various embodiments, any number of actions may be used as a trigger to initiate the interaction between the user smart device and the kiosk. In one example, similar to users' smart device to smart device sensing, for BLE the interaction between the user smart device and kiosk may begin after a signal strength exceeds a threshold. For UWB and ZigBee, the interaction may begin after the physical distance between the smart device and the kiosk is less than a threshold distance (e.g. 20 feet, 10 feet, 5 feet, or the like). Such embodiments are examples of a triggering effect based upon proximity. In additional embodiments, as the user walks away from the kiosk, when the signal strength drops or the distances exceeds a threshold, the connection between the smart device and kiosk may be terminated.

In additional embodiments, an initiating action may be based upon specific user actions, when the smart device is within communication range of the kiosk. In one example it may be determined by sensors (e.g. accelerometers, etc.) of the smart device that the that the user is holding their smart device and gesturing with it. In some cases, the user may be waving their smart device toward the kiosk, holding their smart device close-to the kiosk (e.g. a tap-in action), and the like. In response to such gestures, the smart device may initiate communication with the kiosk. In other examples, the user may open an application upon their smart phone and select a check-in icon or the like to initiate the interaction. In additional embodiments, after the check-in process of the user, the connection between the smart device and kiosk may be terminated.

In still other embodiments, additional identity reader/sensors may be provided that are coupled to the kiosk. The identity sensors may be used along with known positions of such identity sensors to create a sensing zone. For example, four sensors (e.g. identity readers) are provided in the upper four corners of a room. If only two of the identity sensors can sense the user, it is likely that the user is outside the room, and the kiosk will not be notified. If all four of the identity sensors can sense the user with roughly equal signal strengths or roughly equal distances, it is likely that the user is in the center of the room. In some examples, if the user is determined to be within the room, the interaction between the kiosk and the user device may be initiated.

In additional embodiments, other types of sensors than an identity reader or sensor may be used to initiate the interaction between the smart device. For example, an electronic eye, a magnetic sensor on a door, an ultrasonic or infrared sensor, or the like may be provided and be triggered by presence of a user within a specific area. In such embodiments, when the user triggers one or more of the sensors, the kiosk may be notified and then begin the process of interacting with the user device. Such embodiments may be energy efficient, as the kiosk may not be broadcasting advertisement signals until a user enters the relevant. When the sensors no longer detect the user, the kiosk may be placed back into a power savings mode.

In addition, for a kiosk, as described immediately above, a status flag or bit may be passed from the user's smart device to the kiosk or tablet that indicates whether the contact logging application is running or not. In one example, if the contact logging application is not running, the tablet may display a request to run the application and to check-in again. If the user's device does not run the application, an indication may be sent to a human resources, health resources, building resources, or other administrator associated with the organization.

In still other embodiments, another status bit may be provided to indicate whether the user's health has been "normal" for the last two weeks, or the like. In such cases, if the user's health is not normal, the tablet may display a request for the user to visit a health department, doctor, or the like. In some embodiments, the abnormal health condition may also be sent to a human resources, health resources, building resources, or other administrator associated with the organization.

In some cases, to add additional health screening capability, the kiosk, check-in tablet, or the like may include health screening functionality. In some cases, a temperature sensor (e.g. FLIR, non-contact sensor) may be used; a pulse oximeter (capturing heartbeat rate, oxygen percentage, and the like) may be used; a video camera (capturing heart rate, breathing rate); and the like. These types of readings may be compared to threshold values, and if there is an anomaly, the user may be made aware of it. It is expected that many anomalies are normal, for example a person coming back from a run will likely have a higher heartbeat rate and higher breathing rate, a person coming back from a walk on a sunny day will have a higher temperature, and the like. However, if there is a consistent abnormal reading (e.g. accelerated heart rate) captured from such sensors over time (e.g. two to three days), the user (and/or third parties, e.g. HR administrator) may be notified of the abnormal readings. In various embodiments, the time periods may be determined by a system administrator.

In still other embodiments, a third-party certification may also be used to determine whether a user will be able to enter the building, log into a computer, or the like. In various embodiments, a third-party certification may be stored on the user's smart device and provided in addition to a token, ephemeral ID, or the like to an identity reader device, kiosk, or the like. If no certification is provided, the peripheral will not operate, the user will be displayed a notice, or the like. In other embodiments, the third-party certification may be provided by a server coupled to the authentication server. In one case, if the user is authorized, but no third-party certification (e.g. vaccinated) is given, a token will not be issued by authentication server. In other cases, the token and a flag bit may be provided to the user's smart device, which then provides the token and flag bit to the identity reader device, kiosk, or the like. If the flag bit indicates no certification (e.g. not vaccinated), the peripheral may not operate, the user will be notified, and the like.

As described above, various embodiments are directed towards providing mechanisms for promoting use of contact logging applications and for promoting social distancing. Benefits to such systems include the reduction of computational resources and the greater utilization of existing systems. For example, by limiting which ephemeral IDs are logged based upon signal strength or distance and time, the smart device may have lower storage requirements (or increasing the number of ephemeral IDs that may be stored), may have to upload data less frequently (saving time and energy), and the like. Additionally, by being able to restrict entry for users who may have health anomalies or to provide early notice to those users who may have health anomalies, less back-end contact tracing will have to be performed in case of a health issue.

Therefore, it is to be understood that the present disclosure is not to be limited to the specific examples illustrated and that modifications and other examples are intended to be included within the scope of the appended claims. Moreover, although the foregoing description and the associated drawings describe examples of the present disclosure in the context of certain illustrative combinations of elements and/or functions, it should be appreciated that different combinations of elements and/or functions may be provided by alternative implementations without departing from the scope of the appended claims. Accordingly, parenthetical reference numerals in the appended claims are presented for illustrative purposes only and are not intended to limit the scope of the claimed subject matter to the specific examples provided in the present disclosure.

Further embodiments can be envisioned to one of ordinary skill in the art after reading this disclosure. In other embodiments, combinations or sub-combinations of the above disclosed invention can be advantageously made. The block diagrams of the architecture and flow charts are grouped for ease of understanding. However, it should be understood that combinations of blocks, additions of new blocks, re-arrangement of blocks, and the like are contemplated in alternative embodiments of the present invention.

The specification and drawings are, accordingly, to be regarded in an illustrative rather than a restrictive sense. It will, however, be evident that various modifications and changes may be made thereunto without departing from the broader spirit and scope of the invention as set forth in the claims. More specifically, the claims provide additional disclosure regarding contemplated additional methods of operation, methods for fabrication, additional components and functionalities, and apparatus according to various embodiments of the present invention. More specifically, the claims provide additional disclosure regarding contemplated additional methods of operation, additional components and functionalities, and apparatus according to various embodiments of the present invention.

We claim:

1. A system for monitoring presence comprising:
a plurality of stationary beacons within a physical region, wherein a stationary beacon from the plurality of stationary beacons comprises:
a short-range transceiver configured to transmit a unique advertisement signal to a plurality of smart devices, wherein the plurality of smart devices includes a first smart device and a second smart device, wherein the short-range transceiver is configured to receive a plurality of ephemeral IDs that are not permanently associated with the plurality of smart devices, wherein the plurality of ephemeral IDs includes a first ephemeral ID from the first smart device and a second ephemeral ID from the second smart device, wherein the short-range transceiver is configured to transmit a unique beacon identifier to the plurality of smart devices;
a memory coupled to the first short-range transceiver, configured to store stationary beacon data including: the first ephemeral ID, a first time associated with receipt of the first ephemeral ID, the second ephemeral ID, and a second time associated with receipt of the second ephemeral ID;
a processor coupled to the short-range transceiver and the memory, and
a wide-area interface coupled to the memory, wherein the wide-area interface is configured to transmit the stationary beacon data to an authentication service; and
the authentication service coupled to the plurality of stationary beacons and to the plurality of smart devices, wherein the authentication service is configured to store the stationary beacon data, wherein the authentication service is configured store association data comprising associations among the plurality of ephemeral IDs, the plurality of smart devices and unique beacon identifiers, wherein the authentication service is configured to receive an alert notice from the first smart device, wherein the authentication service is configured to identify the stationary beacon in response to the alert notice and to the association data, wherein the authentication service is configured to determine the second ephemeral ID in response to the stationary beacon data, wherein the authentication service is configured to determine the second smart device in response to the second ephemeral ID and to the association data, and wherein the authentication service is configured to provide an exposure notice to the second smart device.

2. The system of claim 1
wherein the authentication service is configured to determine the second ephemeral ID in response to the stationary beacon data comprises wherein the authentication service is configured to determine the second ephemeral ID in response to the first time being within a period of time relative to the second time.

3. The system of claim 1 where the period of time is selected from a group consisting of: the first time being before the second time by ten minutes or less, and the first time being before or after the second time by five minutes or less.

4. The system of claim 1
wherein the short-range transceiver of the stationary beacon is configured to repeatedly receive first ephemeral ID signals from the first smart device in response to the first smart device being in a vicinity of the stationary beacon;
wherein the short-range transceiver of the stationary beacon is configured to repeatedly receive second ephemeral ID signals from the second smart device in response to the second smart device being in the vicinity of the stationary beacon;
wherein the processor of the stationary beacon is configured to determine a first presence time the first smart device is in the vicinity of the stationary beacon in response to the repeated first ephemeral ID signals;
wherein the processor of the stationary beacon is configured to determine a second presence time the second smart device is in the vicinity of the stationary beacon in response to the repeated second ephemeral ID signals; and
wherein the beacon data also comprises the first presence time and the second presence time.

5. The system of claim 1 wherein the authentication service is configured to determine the second ephemeral ID in response to the stationary beacon data comprises wherein the authentication service is configured to determine the second ephemeral ID in response to the first presence time exceeding a first threshold time period.

6. The system of claim 1 wherein the authentication service is also configured to determine the second ephemeral ID in response to the second presence time exceeding a second threshold time period.

7. The system of claim 1
wherein the stationary beacon is coupled to a peripheral device;
wherein the short-range transceiver of the stationary beacon is also configured to receive a token from the first smart device derived from the authentication service;
wherein the processor or the stationary beacon is also configured to determine if the token is valid;
wherein the processor is configured to direct the peripheral device to perform a physical action in response to the token being determined to be valid; and
wherein the physical action is selected from a group consisting of: deactivating an electromagnet device, opening a gate, allowing a door to open, enabling a control panel, unlatching a latch, enabling a computing device, logging into a user account or service, providing a good, providing a receipt.

8. The system of claim 1 wherein the short-range transceiver is selected from a group of devices consisting of: Bluetooth Low Energy (BLE), Ultrawide band (UWB), Zigbee and NFC.

9. A method for a system comprising:
receiving with a first transceiver of a first smart device, an advertisement signal from a stationary beacon;
outputting with the first transceiver of the first smart device, a first ephemeral ID that is not permanently associated with the first smart device, to the stationary beacon;
receiving with the first transceiver of the first smart device, a beacon identifier from a stationary beacon;
outputting with a second transceiver of the first smart device, the first ephemeral ID, a first user identifier and the beacon identifier to an authentication service; and
storing in an association log in the authentication service, the first ephemeral ID, the first user identifier and the beacon identifier; and
storing in a beacon log in the authentication service, a log of the stationary beacon including the first ephemeral ID.

10. The method of claim 9 further comprising:
receiving with a third transceiver of a second smart device, the advertisement signal from the stationary beacon;
outputting with the third transceiver of the second smart device, a second ephemeral ID that is not permanently associated with the second smart device, to the stationary beacon;
receiving with the third transceiver of the second smart device, the beacon identifier from the stationary beacon;
outputting with a fourth transceiver of the second smart device, the second ephemeral ID, a second user identifier and the beacon identifier to the authentication service; and
storing in the association log in the authentication service, the second ephemeral ID, the second user identifier and the beacon identifier; and
storing in the stationary beacon the first ephemeral ID and the second ephemeral ID;
providing from the stationary beacon, beacon data including the first ephemeral ID, the second ephemeral ID and the beacon identifier to the authentication server; and
storing in the association log in the authentication service, a beacon log comprising the beacon data.

11. The method of claim 10 further comprising:
receiving with an input portion of the first smart device, an alert notice;
outputting with the second transceiver of the first smart device, the first user identifier and the alert notice to the authentication server;
determining in the authentication service, the beacon identifier in response to the first user identifier and the association log;

determining in the authentication service, the second user identifier in response to the determination of the beacon identifier, the association log and the beacon log; and outputting from the authentication service, another alert notice to the second smart device in response to the determining of the second user identifier.

12. The method of claim 10 wherein the receiving with the first transceiver of the first smart device, the beacon identifier occurs at a first time;

wherein the outputting with the second transceiver of the first smart device further comprises outputting with the second transceiver, the first time to the authentication service;

wherein the storing in the association log in the authentication service further comprises storing in the association log in the authentication service, the first time;

wherein the receiving with the third transceiver of the second smart device, the beacon identifier occurs at a second time;

wherein the outputting with the fourth transceiver of the second smart device further comprises outputting with the fourth transceiver, the second time to the authentication service; and wherein the storing in the association log in the authentication service further comprises storing in the association log in the authentication service, the second time.

13. The method of claim 12 further comprising:

receiving with an input portion of the first smart device, an alert notice;

outputting with the second transceiver of the first smart device, the first user identifier and the alert notice to the authentication server;

determining in the authentication service, the beacon identifier in response to the first user identifier and the association log;

determining in the authentication service whether the second time is after the first time;

determining in the authentication service, the second user identifier in response to the determination of the beacon identifier, the association log, and a determination that the second time is after the first time;

outputting from the authentication service, another alert notice to the second smart device in response to the determining of the second user identifier; and inhibiting outputting from the authentication service, another alert notice to the second smart device in response to a determination that the second time is not after the first time.

14. The method of claim 10 further comprising:

storing in the stationary beacon a first time associated with the first ephemeral ID and a second time associated with the second ephemeral ID; and providing from the stationary beacon, the beacon data including the first ephemeral ID, the second ephemeral ID, the beacon identifier, the first time and the second time to the authentication server.

15. The method of claim 9 wherein the first ephemeral ID comprises a MAC address not permanently associated with the first smart device.

16. A method for monitoring electronic contacts comprising:

outputting with the first transceiver of a first smart device, a first ephemeral ID that is not permanently associated with the first smart device but not a first user identifier that is associated with the first smart device, to a second smart device;

outputting with a second transceiver of the second smart device, a second ephemeral ID that is not permanently associated with the second smart device but not a second user identifier that is associated with the second smart device, to the first smart device;

outputting with a third transceiver of the first smart device, the first ephemeral ID, the first user identifier and the second ephemeral ID to an authentication service in response to the second ephemeral ID;

outputting with a fourth transceiver of the second smart device, the second ephemeral ID, the second user identifier, and the first ephemeral ID to the authentication service in response to the first ephemeral ID; and storing in the authentication service an association log comprising first associations between: the first ephemeral ID and the first user identifier, the first ephemeral ID and the second ephemeral ID, and the second ephemeral ID and the second user identifier.

17. The method of claim 16 further comprising:

outputting with the first transceiver of the first smart device, a third ephemeral ID that is not permanently associated with the first smart device but not the first user identifier, to a third smart device;

outputting with a fifth transceiver of the third smart device, a fourth ephemeral ID that is not permanently associated with the third smart device but not a third user identifier that is associated with the third smart device, to the first smart device;

outputting with the third transceiver of the first smart device, the third ephemeral ID, the first user identifier and the fourth ephemeral ID to the authentication service in response to the fourth ephemeral ID;

outputting with a sixth transceiver of the third smart device, the fourth ephemeral ID, the third user identifier, and the third ephemeral ID to the authentication service in response to the first ephemeral ID; and storing in the authentication service the association log comprising second associations between: the third ephemeral ID and the first user identifier, the third ephemeral ID and the fourth ephemeral ID, and the fourth ephemeral ID and the third user identifier.

18. The method of claim 17 further comprising:

receiving with an input portion of the first smart device, an alert notice;

outputting with the third transceiver of the first smart device, the first user identifier to the authentication server, in response to the alert notice;

determining in the authentication service, the second user identifier in response to the first user identifier and the association log; and outputting from the authentication service, an alert notice to the second smart device in response to the determining of the second user identifier.

19. The method of claim 18 further comprising:

determining in the authentication service, the fourth user identifier in response to the first user identifier and the association log; and outputting from the authentication service, another alert notice to the third smart device in response to the determining of the fourth user identifier.

20. The method of claim 19 wherein the outputting from the authentication service, another alert notice to the third smart device comprises sending a text message from the authentication service to the third smart device.

* * * * *